(12) United States Patent
Labrecque et al.

(10) Patent No.: US 10,869,902 B2
(45) Date of Patent: *Dec. 22, 2020

(54) CURED GEL AND METHOD OF MAKING

(71) Applicant: Atrium Medical Corporation, Merrimack, NH (US)

(72) Inventors: Roger Labrecque, Londonderry, NH (US); Philip McNamara, Concord, NH (US); Joseph Ferraro, Londonderry, NH (US); Lisa Rogers, Londonderry, NH (US); Paul Martakos, Pelham, NH (US); Theodore Karwoski, Hollis, NH (US); Steve A. Herweck, Nashua, NH (US); Keith M. Faucher, Nashua, NH (US); Thomas M. Swanick, Hillsborough, NH (US)

(73) Assignee: ATRIUM MEDICAL CORPORATION, Merrimack, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/841,993

(22) Filed: Dec. 14, 2017

(65) Prior Publication Data
US 2018/0200306 A1   Jul. 19, 2018

Related U.S. Application Data

(60) Division of application No. 14/511,765, filed on Oct. 10, 2014, now Pat. No. 10,016,465, which is a
(Continued)

(51) Int. Cl.
| | | |
|---|---|---|
| A61K 47/14 | (2017.01) |
| A61K 47/22 | (2006.01) |
| A61L 31/08 | (2006.01) |
| A61L 31/16 | (2006.01) |
| A61K 35/60 | (2006.01) |
| A61F 13/02 | (2006.01) |
| A61K 9/00 | (2006.01) |
| A61K 9/06 | (2006.01) |
| A61K 31/225 | (2006.01) |
| A61K 31/355 | (2006.01) |
| A61K 47/12 | (2006.01) |
| A61L 2/07 | (2006.01) |
| A61L 2/08 | (2006.01) |
| A61L 2/20 | (2006.01) |
| A61L 31/00 | (2006.01) |
| A61L 31/10 | (2006.01) |
| A61L 31/14 | (2006.01) |

(Continued)

(52) U.S. Cl.
CPC .............. *A61K 35/60* (2013.01); *A61F 13/02* (2013.01); *A61F 13/023* (2013.01); *A61K 9/0024* (2013.01); *A61K 9/06* (2013.01); *A61K 31/225* (2013.01); *A61K 31/355* (2013.01); *A61K 38/13* (2013.01); *A61K 47/12* (2013.01); *A61K 47/14* (2013.01); *A61L 2/07* (2013.01); *A61L 2/081* (2013.01); *A61L 2/087* (2013.01); *A61L 2/206* (2013.01); *A61L 2/208* (2013.01); *A61L 27/36* (2013.01); *A61L 27/3604* (2013.01); *A61L 27/52* (2013.01); *A61L 27/54* (2013.01); *A61L 31/005* (2013.01); *A61L 31/10* (2013.01); *A61L 31/145* (2013.01); *A61F 2/06* (2013.01); *A61F 2250/0067* (2013.01); *A61L 2202/24* (2013.01); *A61L 2300/22* (2013.01); *A61L 2300/252* (2013.01); *A61L 2300/404* (2013.01); *A61L 2300/41* (2013.01); *A61L 2300/414* (2013.01); *A61L 2300/42* (2013.01); *A61L 2300/602* (2013.01); *B05D 3/067* (2013.01)

(58) Field of Classification Search
CPC ......... A61K 47/14; A61K 47/22; A61L 31/08; A61L 31/16; A61L 31/148; A61L 2300/22; A61L 2300/428; A61L 2300/606; A61L 2420/02; A61M 1/12; A61F 2250/0067
USPC ........................................................ 424/523
See application file for complete search history.

(56) References Cited

U.S. PATENT DOCUMENTS

| | | |
|---|---|---|
| 1,948,959 A | 2/1934 | Croce |
| 2,368,306 A | 1/1945 | Kiefer et al. |

(Continued)

FOREIGN PATENT DOCUMENTS

| | | |
|---|---|---|
| CN | 1360951 A | 7/2002 |
| CN | 1429559 A | 7/2003 |

(Continued)

OTHER PUBLICATIONS

Oliveira, Fernanda L.C., et al., Triglyceride Hydrolysis of Soy Oil vs Fish Oil Emulsions, Journal of Parenteral and Enteral Nutrition, Jul./Aug. 1997, 224-229, vol. 21, No. 4.

(Continued)

*Primary Examiner* — Michael G. Hartley
*Assistant Examiner* — Nabila G Ebrahim
(74) *Attorney, Agent, or Firm* — Wesley Scott Ashton

(57) ABSTRACT

A cured non-polymeric gel including a plurality of non-polymeric cross-links. The non-polymeric cross-links result from curing an oil or oil composition at selected curing conditions to achieve a desired amount of cross-linking to form the non-polymeric gel. The desired amount of cross-linking is selected based on a desired rate of degradation of the gel after the gel is implanted. The oil or oil composition comprises one or more of eicosapentaenoic acid (EPA), docosahexaenoic acid (DHA), or alpha-linolenic acid (ALA).

11 Claims, 10 Drawing Sheets

Related U.S. Application Data continuation of application No. 11/237,263, filed on Sep. 28, 2005, now Pat. No. 8,858,978.

(60) Provisional application No. 60/613,808, filed on Sep. 28, 2004.

(51) Int. Cl.
  A61L 27/36 (2006.01)
  A61L 27/52 (2006.01)
  A61L 27/54 (2006.01)
  A61K 38/13 (2006.01)
  A61F 2/06 (2013.01)
  B05D 3/06 (2006.01)

(56) References Cited

U.S. PATENT DOCUMENTS

| | | |
|---|---|---|
| 2,403,458 A | 7/1946 | Ransom |
| 2,555,976 A | 6/1951 | Keenan et al. ............ C09F 7/02 554/26 |
| 2,735,814 A | 2/1956 | Hodson et al. |
| 2,986,540 A | 5/1961 | Posnansky |
| 3,328,259 A | 6/1967 | Anderson |
| 3,464,413 A | 9/1969 | Goldfarb et al. |
| 3,556,294 A | 1/1971 | Walck et al. |
| 3,567,820 A | 3/1971 | Sperti |
| 3,803,109 A | 4/1974 | Nemoto et al. |
| 3,967,728 A | 7/1976 | Gordon et al. |
| 4,185,637 A | 1/1980 | Mattei |
| 4,308,120 A | 12/1981 | Pennewiss et al. |
| 4,323,547 A | 4/1982 | Knust et al. |
| 4,345,414 A | 8/1982 | Bornat et al. |
| 4,447,418 A | 5/1984 | Maddoux |
| 4,557,925 A | 12/1985 | Lindahl et al. |
| 4,655,221 A | 4/1987 | Devereux |
| 4,664,114 A | 5/1987 | Ghodstain |
| 4,702,252 A | 10/1987 | Brooks et al. |
| 4,711,902 A | 12/1987 | Serno |
| 4,733,665 A | 3/1988 | Palmaz |
| 4,769,038 A | 9/1988 | Bendavid et al. |
| 4,813,210 A | 3/1989 | Masuda et al. |
| 4,814,329 A | 3/1989 | Harsanyi et al. |
| 4,824,436 A | 4/1989 | Wolinsky |
| 4,846,844 A | 4/1989 | De Leon et al. |
| 4,847,301 A | 7/1989 | Murray |
| 4,880,455 A | 11/1989 | Blank |
| 4,883,667 A | 11/1989 | Eckenhoff |
| 4,886,787 A | 12/1989 | De Belder et al. |
| 4,894,231 A | 1/1990 | Moreau et al. |
| 4,895,724 A | 1/1990 | Cardinal et al. |
| 4,911,707 A | 3/1990 | Heiber et al. |
| 4,937,254 A | 6/1990 | Sheffield et al. |
| 4,938,763 A | 7/1990 | Dunn et al. |
| 4,941,308 A | 7/1990 | Grabenkort et al. |
| 4,941,877 A | 7/1990 | Montano, Jr. |
| 4,947,840 A | 8/1990 | Yannas et al. |
| 4,952,419 A | 8/1990 | de Leon |
| 4,968,302 A | 11/1990 | Schluter et al. |
| 4,994,033 A | 2/1991 | Shockey et al. |
| 5,017,229 A | 5/1991 | Burns et al. |
| 5,041,125 A | 8/1991 | Montano, Jr. |
| 5,049,132 A | 9/1991 | Shaffer et al. |
| 5,061,281 A | 10/1991 | Mares et al. |
| 5,071,609 A | 12/1991 | Tu et al. |
| 5,087,244 A | 2/1992 | Wolinsky et al. |
| 5,087,246 A | 2/1992 | Smith |
| 5,102,402 A | 4/1992 | Dror et al. |
| 5,118,493 A | 6/1992 | Kelley et al. |
| 5,132,115 A | 7/1992 | Wolter et al. |
| 5,147,374 A | 9/1992 | Fernandez |
| 5,151,272 A | 9/1992 | Engstrom et al. |
| 5,171,148 A | 12/1992 | Wasserman et al. |
| 5,179,174 A | 1/1993 | Elton |
| 5,199,951 A | 4/1993 | Spears |
| 5,202,310 A | 4/1993 | Levy et al. |
| 5,206,077 A | 4/1993 | Cowley et al. |
| 5,176,956 A | 5/1993 | Jevne et al. |
| 5,254,105 A | 10/1993 | Haaga |
| 5,267,985 A | 12/1993 | Shimada et al. |
| 5,279,565 A | 1/1994 | Klein et al. |
| 5,282,785 A | 2/1994 | Shapland et al. |
| 5,283,257 A | 2/1994 | Gregory et al. |
| 5,286,254 A | 2/1994 | Shapland et al. |
| 5,295,962 A | 3/1994 | Crocker et al. |
| 5,304,121 A | 4/1994 | Sahatjian |
| 5,336,178 A | 8/1994 | Kaplan et al. |
| 5,356,432 A | 10/1994 | Rutkow et al. |
| 5,368,602 A | 11/1994 | de la Torre |
| 5,371,109 A | 12/1994 | Engstrom et al. |
| 5,380,328 A | 1/1995 | Morgan |
| 5,387,658 A | 2/1995 | Schroder et al. |
| 5,403,283 A | 4/1995 | Luther |
| 5,411,951 A | 5/1995 | Mitchell |
| 5,411,988 A | 6/1995 | Bochow et al. |
| 5,447,940 A | 9/1995 | Harvey et al. |
| 5,456,666 A | 10/1995 | Campbell et al. |
| 5,456,720 A | 10/1995 | Schultz et al. |
| 5,458,568 A | 10/1995 | Racchini et al. |
| 5,458,572 A | 10/1995 | Racchini et al. |
| 5,464,650 A | 11/1995 | Berg et al. |
| 5,468,242 A | 11/1995 | Reisberg |
| 5,480,436 A | 1/1996 | Bakker et al. |
| 5,480,653 A | 1/1996 | Aguadish et al. |
| 5,490,839 A | 2/1996 | Wang et al. |
| 5,498,238 A | 3/1996 | Shapland et al. |
| 5,499,971 A | 3/1996 | Shapland et al. |
| 5,509,899 A | 4/1996 | Fan et al. |
| 5,514,092 A | 5/1996 | Forman et al. |
| 5,547,677 A | 8/1996 | Wright |
| 5,549,901 A | 8/1996 | Wright |
| 5,558,071 A | 9/1996 | Ward et al. |
| 5,569,198 A | 10/1996 | Racchini |
| 5,579,149 A | 11/1996 | Moret et al. |
| 5,573,781 A | 12/1996 | Brown et al. |
| 5,580,923 A | 12/1996 | Yeung et al. |
| 5,589,508 A | 12/1996 | Schlotzer et al. |
| 5,591,230 A | 1/1997 | Horn et al. |
| 5,593,441 A | 1/1997 | Lichtenstein et al. |
| 5,603,721 A | 2/1997 | Lau et al. |
| 5,605,696 A | 2/1997 | Eury et al. |
| 5,612,074 A | 3/1997 | Leach |
| 5,614,284 A | 3/1997 | Kranzler et al. |
| 5,627,077 A | 5/1997 | Dyllick-Brenzinger et al. |
| 5,628,730 A | 5/1997 | Shapland et al. |
| 5,629,021 A | 5/1997 | Wright |
| 5,634,899 A | 6/1997 | Shapland et al. |
| 5,634,931 A | 6/1997 | Kugel |
| 5,637,113 A | 6/1997 | Tartagalia et al. |
| 5,637,317 A | 6/1997 | Hans |
| 5,641,767 A | 6/1997 | Wess et al. |
| 5,665,115 A | 9/1997 | Cragg |
| 5,693,014 A | 12/1997 | Abele et al. |
| 5,695,525 A | 12/1997 | Mulhauser et al. |
| 5,700,286 A | 12/1997 | Tartagalia et al. |
| 5,700,848 A | 12/1997 | Soon-Shiong |
| 5,705,485 A | 1/1998 | Cini |
| 5,731,346 A | 3/1998 | Egberg et al. |
| 5,736,152 A | 4/1998 | Dunn |
| 5,738,869 A | 4/1998 | Fischer et al. |
| 5,747,533 A | 5/1998 | Egberg et al. |
| 5,749,845 A | 5/1998 | Hildebrand et al. |
| 5,753,259 A | 5/1998 | Engstrom et al. |
| 5,760,081 A | 6/1998 | Leaf et al. |
| 5,766,246 A | 6/1998 | Mulhauser et al. |
| 5,766,710 A | 6/1998 | Turnlund et al. |
| 5,789,465 A | 8/1998 | Harvey et al. |
| 5,800,392 A | 9/1998 | Racchini |
| 5,807,306 A | 9/1998 | Shapland et al. |
| 5,817,343 A | 10/1998 | Burke |
| 5,824,082 A | 10/1998 | Brown |
| 5,827,325 A | 10/1998 | Landgrebe et al. |
| 5,828,785 A | 10/1998 | Kitsuki |
| 5,837,313 A | 11/1998 | Ding et al. |

(56) References Cited

U.S. PATENT DOCUMENTS

| | | |
|---|---|---|
| 5,843,172 A | 12/1998 | Yan |
| 5,843,919 A | 12/1998 | Burger |
| 5,865,787 A | 2/1999 | Shapland et al. |
| 5,874,470 A | 2/1999 | Nehne et al. |
| 5,879,359 A | 3/1999 | Dorigatti et al. |
| 5,897,911 A | 4/1999 | Loeffler |
| 5,898,040 A | 4/1999 | Shalaby et al. |
| 5,902,266 A | 5/1999 | Leone et al. |
| 5,906,831 A | 5/1999 | Larsson et al. |
| 5,931,165 A | 8/1999 | Reich et al. |
| 5,947,977 A | 9/1999 | Slepian et al. |
| 5,954,767 A | 9/1999 | Pajotin et al. |
| 5,955,502 A | 9/1999 | Hansen et al. |
| 5,986,043 A | 11/1999 | Hubbell et al. |
| 6,004,549 A | 12/1999 | Reichert et al. |
| 6,005,004 A | 12/1999 | Katz et al. |
| 6,010,480 A | 1/2000 | Abele et al. |
| 6,010,766 A | 1/2000 | Braun et al. |
| 6,010,776 A | 1/2000 | Exsted et al. |
| 6,013,055 A | 1/2000 | Bampos et al. |
| 6,015,844 A | 1/2000 | Harvey et al. |
| 6,028,164 A | 2/2000 | Loomis |
| 6,033,380 A | 3/2000 | Butaric et al. |
| 6,033,436 A | 3/2000 | Steinke et al. |
| 6,040,330 A | 3/2000 | Hausheer et al. |
| 6,048,332 A | 4/2000 | Duffy et al. |
| 6,048,725 A | 4/2000 | Shimada et al. |
| 6,056,970 A | 5/2000 | Greenawalt et al. |
| 6,066,777 A | 5/2000 | Benchetrit |
| 6,075,180 A | 6/2000 | Sharber et al. |
| 6,077,698 A | 6/2000 | Swan et al. |
| 6,080,442 A | 6/2000 | Yoshikawa et al. |
| 6,083,950 A | 7/2000 | Anand et al. |
| 6,090,809 A | 7/2000 | Anand et al. |
| 6,093,792 A | 7/2000 | Gross et al. |
| 6,117,911 A | 9/2000 | Grainger et al. |
| 6,120,477 A | 9/2000 | Campbell et al. |
| 6,120,539 A | 9/2000 | Eldridge et al. |
| 6,120,789 A | 9/2000 | Dunn |
| 6,132,765 A | 10/2000 | DiCosmo et al. |
| 6,146,358 A | 11/2000 | Rowe |
| 6,152,944 A | 11/2000 | Holman et al. |
| 6,176,863 B1 | 1/2001 | Kugel et al. |
| 6,193,746 B1 | 2/2001 | Strecker |
| 6,197,357 B1 | 3/2001 | Lawton et al. |
| 6,200,985 B1 | 3/2001 | Cottens et al. |
| 6,203,551 B1 | 3/2001 | Wu |
| 6,206,916 B1 | 3/2001 | Furst |
| 6,211,315 B1 | 4/2001 | Larock et al. |
| 6,224,579 B1 | 5/2001 | Modak et al. |
| 6,224,909 B1 | 5/2001 | Opitz et al. |
| 6,228,383 B1 | 5/2001 | Hansen et al. |
| 6,229,032 B1 | 5/2001 | Jacobs et al. |
| 6,231,600 B1 | 5/2001 | Zhong |
| 6,245,366 B1 | 6/2001 | Popplewell et al. |
| 6,245,811 B1 | 6/2001 | Harrobin et al. |
| 6,258,124 B1 | 6/2001 | Darois et al. |
| 6,254,634 B1 | 7/2001 | Anderson et al. |
| 6,262,109 B1 | 7/2001 | Clark et al. |
| 6,273,913 B1 | 8/2001 | Wright et al. |
| 6,284,268 B1 | 9/2001 | Mishra et al. |
| 6,287,285 B1 | 9/2001 | Michal et al. |
| 6,287,316 B1 | 9/2001 | Agarwal |
| 6,299,604 B1 | 10/2001 | Ragheb et al. |
| 6,306,438 B1 | 10/2001 | Oshlack et al. |
| 6,326,072 B1 | 12/2001 | Ojeda et al. |
| 6,326,360 B1 | 12/2001 | Kanazawa et al. |
| 6,331,568 B1 | 12/2001 | Horrobin |
| 6,342,254 B1 | 1/2002 | Soudant et al. |
| 6,346,110 B2 | 2/2002 | Wu |
| 6,355,063 B1 | 3/2002 | Calcote |
| 6,358,556 B1 | 3/2002 | Ding et al. |
| 6,364,856 B1 | 4/2002 | Ding et al. |
| 6,364,893 B1 | 4/2002 | Sahatjian et al. |
| 6,364,903 B2 | 4/2002 | Tseng et al. |
| 6,368,541 B1 | 4/2002 | Pajotin et al. |
| 6,368,658 B1 | 4/2002 | Schwarz et al. |
| 6,369,039 B1 | 4/2002 | Palasis et al. |
| 6,387,301 B1 | 5/2002 | Nakajima et al. |
| 6,387,379 B1 | 5/2002 | Goldberg et al. |
| 6,410,587 B1 | 6/2002 | Grainger et al. |
| 6,444,318 B1 | 9/2002 | Guire et al. |
| 6,451,373 B1 | 9/2002 | Hossainy et al. |
| 6,463,323 B1 | 10/2002 | Conrad-Vlasak et al. |
| 6,465,525 B1 | 10/2002 | Guire et al. |
| 6,471,980 B2 | 10/2002 | Sirhan et al. |
| 6,479,683 B1 | 11/2002 | Abney et al. |
| 6,485,752 B1 | 11/2002 | Rein et al. |
| 6,491,938 B2 | 12/2002 | Kunz |
| 6,500,174 B1 | 12/2002 | Maguire |
| 6,500,453 B2 | 12/2002 | Brey et al. |
| 6,503,556 B2 | 1/2003 | Harish et al. |
| 6,506,410 B1 | 1/2003 | Park |
| 6,525,145 B2 | 2/2003 | Gavaert et al. |
| 6,527,801 B1 | 3/2003 | Dutta |
| 6,534,693 B2 | 3/2003 | Fischell et al. |
| 6,541,116 B2 | 4/2003 | Michal et al. |
| 6,544,223 B1 | 4/2003 | Kokish |
| 6,544,224 B1 | 4/2003 | Steese-Bradley |
| 6,548,081 B2 | 4/2003 | Sadozai et al. |
| 6,565,659 B1 | 5/2003 | Pacetti et al. |
| 6,569,441 B2 | 5/2003 | Kunz et al. |
| 6,579,851 B2 | 6/2003 | Goke et al. |
| 6,596,002 B2 | 7/2003 | Therin et al. |
| 6,599,323 B2 | 7/2003 | Melican et al. |
| 6,610,006 B1 | 8/2003 | Amid et al. |
| 6,610,035 B2 | 8/2003 | Yang et al. |
| 6,610,068 B1 | 8/2003 | Yang et al. |
| 6,616,650 B1 | 9/2003 | Rowe |
| 6,630,151 B1 | 10/2003 | Tarletsky et al. |
| 6,630,167 B2 | 10/2003 | Zhang |
| 6,632,822 B1 | 10/2003 | Rickards et al. |
| 6,641,611 B2 | 11/2003 | Jayaraman |
| 6,645,547 B1 | 11/2003 | Shekalim |
| 6,663,880 B1 | 12/2003 | Roorda et al. |
| 6,669,735 B1 | 12/2003 | Pelissier |
| 6,670,355 B2 | 12/2003 | Azrolan et al. |
| 6,677,342 B2 | 1/2004 | Wolff et al. |
| 6,677,386 B1 | 1/2004 | Giezen et al. |
| 6,685,956 B2 | 2/2004 | Chu et al. |
| 6,689,388 B2 | 2/2004 | Kuhrts |
| 6,696,583 B2 | 2/2004 | Koncar et al. |
| 6,723,133 B1 | 4/2004 | Pajotin |
| 6,730,016 B1 | 5/2004 | Cox et al. |
| 6,730,064 B2 | 5/2004 | Ragheb et al. |
| 6,740,122 B1 | 5/2004 | Pajotin |
| 6,753,071 B1 | 6/2004 | Pacetti |
| 6,758,847 B2 | 7/2004 | Maguire |
| 6,761,903 B2 | 7/2004 | Chen et al. |
| 6,764,509 B2 | 7/2004 | Chinn et al. |
| 6,776,796 B2 | 8/2004 | Falotico et al. |
| 6,794,485 B2 | 9/2004 | Shalaby et al. |
| 6,808,536 B2 | 10/2004 | Wright et al. |
| 6,833,004 B2 | 12/2004 | Ishii et al. |
| 6,852,330 B2 | 2/2005 | Bowman et al. |
| 6,875,230 B1 | 4/2005 | Morita et al. |
| 6,884,428 B2 | 4/2005 | Binette et al. |
| 6,887,270 B2 | 5/2005 | Miller et al. |
| 6,899,729 B1 | 5/2005 | Cox et al. |
| 6,902,522 B1 | 6/2005 | Walsh et al. |
| 6,918,927 B2 | 7/2005 | Bates et al. |
| 6,996,952 B2 | 2/2006 | Gupta et al. |
| 7,070,858 B2 | 7/2006 | Shalaby et al. |
| 7,090,655 B2 | 8/2006 | Barry |
| 7,101,381 B2 | 9/2006 | Ford et al. |
| 7,112,209 B2 | 9/2006 | Ramshaw et al. |
| 7,135,164 B2 | 11/2006 | Rojanapanthu et al. |
| 7,152,611 B2 | 12/2006 | Brown et al. |
| 7,311,980 B1 | 12/2007 | Hossainy et al. |
| 7,323,178 B1 | 1/2008 | Zhang et al. |
| 7,323,189 B2 | 1/2008 | Pathak |
| 7,415,811 B2 | 8/2008 | Gottlieb et al. |
| 7,691,946 B2 | 4/2010 | Liu et al. |
| 7,854,958 B2 | 12/2010 | Kramer |

(56) References Cited

U.S. PATENT DOCUMENTS

| | | |
|---|---|---|
| 7,947,015 B2 | 5/2011 | Herweck et al. |
| 8,001,922 B2 | 8/2011 | Labrecque et al. |
| 8,021,331 B2 | 9/2011 | Herweck et al. |
| 8,124,127 B2 | 2/2012 | Faucher et al. |
| 8,263,102 B2 | 9/2012 | Labrecque et al. |
| 8,298,290 B2 | 10/2012 | Pelissier et al. |
| 8,308,684 B2 | 11/2012 | Herweck et al. |
| 8,312,836 B2 | 11/2012 | Corbeil et al. |
| 8,367,099 B2 | 2/2013 | Herweck et al. |
| 8,461,129 B2 | 6/2013 | Bolduc et al. |
| 8,722,077 B2 | 5/2014 | Labrecque et al. |
| 8,888,887 B2 | 11/2014 | Hargrove et al. |
| 9,000,040 B2 | 4/2015 | Faucher et al. |
| 9,012,506 B2 | 4/2015 | Faucher et al. |
| 9,220,820 B2 | 12/2015 | Faucher et al. |
| 3,278,161 A1 | 3/2016 | Swanick et al. |
| 9,427,423 B2 | 8/2016 | Swanick et al. |
| 9,493,636 B2 | 11/2016 | Ah et al. |
| 2001/0022988 A1 | 9/2001 | Schwarz et al. |
| 2001/0025034 A1 | 9/2001 | Arbiser |
| 2001/0025196 A1 | 9/2001 | Chinn et al. |
| 2001/0026803 A1 | 10/2001 | Tebbe et al. |
| 2001/0027299 A1 | 10/2001 | Yang et al. |
| 2001/0051595 A1 | 12/2001 | Lyons et al. |
| 2002/0002154 A1 | 1/2002 | Guivarch et al. |
| 2002/0007209 A1 | 1/2002 | Scheerder et al. |
| 2002/0012741 A1 | 1/2002 | Heinz et al. |
| 2002/0013590 A1 | 1/2002 | Therin et al. |
| 2002/0015970 A1 | 2/2002 | Murray et al. |
| 2002/0022052 A1 | 2/2002 | Dransfield |
| 2002/0026899 A1 | 3/2002 | McLaughlin et al. |
| 2002/0026900 A1 | 3/2002 | Huang et al. |
| 2002/0032414 A1 | 3/2002 | Ragheb et al. |
| 2002/0055701 A1 | 5/2002 | Fischell et al. |
| 2002/0077652 A1 | 6/2002 | Kieturakis et al. |
| 2002/0082679 A1 | 6/2002 | Sirhan et al. |
| 2002/0098278 A1 | 7/2002 | Bates et al. |
| 2002/0103494 A1 | 8/2002 | Pacey |
| 2002/0116045 A1 | 8/2002 | Eidenschink |
| 2002/0120333 A1 | 8/2002 | Keogh et al. |
| 2002/0122877 A1 | 9/2002 | Harish et al. |
| 2002/0127327 A1 | 9/2002 | Schwarz et al. |
| 2002/0142089 A1 | 10/2002 | Koike et al. |
| 2002/0183716 A1 | 12/2002 | Herweck et al. |
| 2002/0192352 A1 | 12/2002 | Jamshed |
| 2002/0193829 A1 | 12/2002 | Kennedy et al. |
| 2003/0003125 A1 | 1/2003 | Nathan et al. |
| 2003/0003221 A1 | 1/2003 | Zhong et al. |
| 2003/0004564 A1 | 1/2003 | Elkins et al. |
| 2003/0009213 A1 | 1/2003 | Yang |
| 2003/0033004 A1 | 2/2003 | Ishii |
| 2003/0036803 A1 | 2/2003 | McGhan et al. |
| 2003/0055403 A1 | 3/2003 | Nestenborg et al. |
| 2003/0065292 A1 | 4/2003 | Darouiche et al. |
| 2003/0065345 A1 | 4/2003 | Weadock ......... A61B 17/06166 606/153 |
| 2003/0069632 A1 | 4/2003 | De Scheerder et al. |
| 2003/0072784 A1 | 4/2003 | Williams |
| 2003/0077272 A1 | 4/2003 | Pathak |
| 2003/0077310 A1 | 4/2003 | Pathak et al. |
| 2003/0077452 A1 | 4/2003 | Guire et al. |
| 2003/0083740 A1 | 5/2003 | Pathak |
| 2003/0086958 A1 | 5/2003 | Arnold et al. |
| 2003/0094728 A1 | 5/2003 | Tayebi |
| 2003/0100955 A1 | 5/2003 | Greenawalt et al. |
| 2003/0108588 A1 | 6/2003 | Chen et al. |
| 2003/0130206 A1 | 6/2003 | Koziak et al. |
| 2003/0124087 A1 | 7/2003 | Kim et al. |
| 2003/0152609 A1 | 8/2003 | Fischell et al. |
| 2003/0175408 A1 | 9/2003 | Timm et al. |
| 2003/0176915 A1 | 9/2003 | Wright et al. |
| 2003/0181975 A1 | 9/2003 | Ishii et al. |
| 2003/0181988 A1 | 9/2003 | Rousseau |
| 2003/0187516 A1 | 10/2003 | Amid et al. |
| 2003/0191179 A1 | 10/2003 | Joshi-Hangal et al. |
| 2003/0204168 A1 | 10/2003 | Bosma et al. |
| 2003/0204618 A1 | 10/2003 | Foster et al. |
| 2003/0207019 A1 | 11/2003 | Shekalim et al. |
| 2003/0211230 A1 | 11/2003 | Pacetti et al. |
| 2003/0212462 A1 | 11/2003 | Gryska et al. |
| 2003/0220297 A1 | 11/2003 | Berstein et al. |
| 2004/0006296 A1 | 1/2004 | Fischell et al. |
| 2004/0013704 A1 | 1/2004 | Kabra et al. |
| 2004/0014810 A1 | 1/2004 | Horrobin |
| 2004/0018228 A1 | 1/2004 | Fischell et al. |
| 2004/0039441 A1 | 2/2004 | Rowland et al. |
| 2004/0058008 A1 | 3/2004 | Tarcha et al. |
| 2004/0060260 A1 | 4/2004 | Gottlieb et al. |
| 2004/0071756 A1 | 4/2004 | Fischell et al. |
| 2004/0072849 A1 | 4/2004 | Schreiber et al. |
| 2004/0073284 A1 | 4/2004 | Bates et al. |
| 2004/0092969 A1 | 5/2004 | Kumar |
| 2004/0102758 A1 | 5/2004 | Davila et al. |
| 2004/0117007 A1 | 6/2004 | Whitbourne et al. |
| 2004/0123877 A1 | 7/2004 | Brown et al. |
| 2004/0131755 A1 | 7/2004 | Zhong et al. |
| 2004/0133275 A1 | 7/2004 | Mansmann |
| 2004/0137066 A1 | 7/2004 | Jayaraman |
| 2004/0142094 A1 | 7/2004 | Narayanan |
| 2004/0146546 A1 | 7/2004 | Gravett et al. |
| 2004/0153125 A1 | 8/2004 | Roby |
| 2004/0156879 A1 | 8/2004 | Muratoglu et al. |
| 2004/0161464 A1 | 8/2004 | Domb |
| 2004/0167572 A1 | 8/2004 | Roth et al. |
| 2004/0170685 A1 | 9/2004 | Carpenter et al. |
| 2004/0192643 A1 | 9/2004 | Pressato et al. |
| 2004/0137179 A1 | 10/2004 | Shojiro et al. |
| 2004/0215219 A1 | 10/2004 | Eldridge et al. |
| 2004/0224003 A1 | 11/2004 | Schultz |
| 2004/0230176 A1 | 11/2004 | Shanahan et al. |
| 2004/0234574 A9 | 11/2004 | Sawhney et al. |
| 2004/0236278 A1 | 11/2004 | Herweck et al. |
| 2004/0241211 A9 | 12/2004 | Fischell |
| 2004/0256264 A1 | 12/2004 | Israelsson et al. |
| 2005/0010078 A1 | 1/2005 | Jamiolkowski et al. |
| 2005/0025804 A1 | 2/2005 | Heller |
| 2005/0042251 A1 | 2/2005 | Zhang et al. |
| 2005/0084514 A1 | 4/2005 | Shebuski et al. |
| 2005/0095267 A1 | 5/2005 | Campbell et al. |
| 2005/0100655 A1 | 5/2005 | Zhong et al. |
| 2005/0101522 A1 | 5/2005 | Speck et al. |
| 2005/0106206 A1 | 5/2005 | Herweck et al. |
| 2005/0106209 A1 | 5/2005 | Ameri et al. |
| 2005/0112170 A1 | 5/2005 | Hossainy et al. |
| 2005/0113687 A1 | 5/2005 | Herweck et al. |
| 2005/0113849 A1 | 5/2005 | Popadiuk et al. |
| 2005/0124062 A1 | 6/2005 | Subirade |
| 2005/0129787 A1 | 6/2005 | Murad |
| 2005/0154416 A1 | 7/2005 | Herweck et al. |
| 2005/0158361 A1 | 7/2005 | Dhondt et al. |
| 2005/0159809 A1 | 7/2005 | Hezi-Yamit et al. |
| 2005/0165476 A1 | 7/2005 | Furst et al. |
| 2005/0165477 A1 | 7/2005 | Anduiza et al. |
| 2005/0181061 A1 | 8/2005 | Roderick et al. |
| 2005/0182485 A1 | 8/2005 | Falotico et al. |
| 2005/0186244 A1 | 8/2005 | Hunter et al. |
| 2005/0187376 A1 | 8/2005 | Pacetti |
| 2005/0203635 A1 | 9/2005 | Hunter et al. |
| 2005/0203636 A1 | 9/2005 | McFetridge |
| 2005/0223679 A1 | 10/2005 | Gottlieb et al. |
| 2005/0232971 A1 | 10/2005 | Hossainy et al. |
| 2005/0249775 A1 | 11/2005 | Falotico et al. |
| 2005/0283229 A1 | 12/2005 | Dugan et al. |
| 2006/0008501 A1 | 1/2006 | Dhont et al. |
| 2006/0020031 A1* | 1/2006 | Berlin ............... A61K 31/045 514/560 |
| 2006/0036311 A1 | 2/2006 | Nakayama et al. |
| 2006/0112536 A1 | 2/2006 | Herweck et al. |
| 2006/0051544 A1 | 3/2006 | Goldmann |
| 2006/0058737 A1 | 3/2006 | Herweck et al. |
| 2006/0058881 A1 | 3/2006 | Trieu |
| 2006/0064175 A1 | 3/2006 | Pelissier et al. |
| 2006/0067974 A1 | 3/2006 | Labrecque et al. |
| 2006/0067975 A1 | 3/2006 | Labrecque et al. |

(56) References Cited

U.S. PATENT DOCUMENTS

| | | |
|---|---|---|
| 2006/0067976 A1 | 3/2006 | Ferraro et al. |
| 2006/0067977 A1 | 3/2006 | Labrecque et al. |
| 2006/0067983 A1 | 3/2006 | Swanick et al. |
| 2006/0068674 A1 | 3/2006 | Dixit et al. |
| 2006/0078586 A1 | 4/2006 | Ferraro |
| 2006/0083768 A1 | 4/2006 | Labrecque et al. |
| 2006/0088596 A1 | 4/2006 | Labrecque et al. |
| 2006/0093643 A1 | 5/2006 | Stenzel |
| 2006/0110457 A1 | 5/2006 | Labrecque et al. |
| 2006/0121081 A1 | 6/2006 | Labrecque et al. |
| 2006/0124056 A1 | 6/2006 | Behnisch et al. |
| 2006/0134209 A1 | 6/2006 | Labhasetwar et al. |
| 2006/0155361 A1 | 7/2006 | Chou |
| 2006/0188607 A1 | 8/2006 | Schramm et al. |
| 2006/0204738 A1 | 9/2006 | Dubrow et al. |
| 2006/0210701 A1 | 9/2006 | Chappa et al. |
| 2006/0240069 A1 | 10/2006 | Utas et al. |
| 2006/0263330 A1 | 11/2006 | Emeta et al. |
| 2006/0269485 A1 | 11/2006 | Friedman et al. |
| 2006/0246105 A1 | 12/2006 | Molz et al. |
| 2007/0003603 A1 | 1/2007 | Karandikar et al. |
| 2007/0015893 A1 | 1/2007 | Hakuta et al. |
| 2007/0071798 A1 | 3/2007 | Herweck et al. |
| 2007/0084144 A1 | 4/2007 | Labrecque et al. |
| 2007/0093894 A1 | 4/2007 | Darouiche |
| 2007/0141112 A1 | 6/2007 | Falotico et al. |
| 2007/0198040 A1 | 8/2007 | Buevich et al. |
| 2007/0202149 A1 | 8/2007 | Faucher et al. |
| 2007/0212411 A1 | 9/2007 | Fawzy et al. |
| 2007/0218182 A1 | 9/2007 | Schneider et al. |
| 2007/0238697 A1 | 10/2007 | Jackson et al. |
| 2007/0264460 A1 | 11/2007 | Del Tredici |
| 2007/0275074 A1 | 11/2007 | Holm et al. |
| 2007/0276487 A1 | 11/2007 | Carteron et al. |
| 2007/0280986 A1 | 12/2007 | Gil et al. |
| 2007/0286891 A1 | 12/2007 | Kettlewell et al. |
| 2007/0299538 A1 | 12/2007 | Roeber |
| 2008/0016037 A1 | 1/2008 | Enomoto et al. |
| 2008/0038307 A1 | 2/2008 | Hoffmann |
| 2008/0044481 A1 | 2/2008 | Harel |
| 2008/0045557 A1 | 2/2008 | Grainger et al. |
| 2008/0071385 A1 | 3/2008 | Binette et al. |
| 2008/0086216 A1 | 4/2008 | Wilson et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0160307 A1 | 7/2008 | Bauchet |
| 2008/0206305 A1 | 8/2008 | Herweck et al. |
| 2008/0207756 A1 | 8/2008 | Herweck et al. |
| 2008/0279929 A1 | 11/2008 | Devane et al. |
| 2008/0286440 A1 | 11/2008 | Scheer et al. |
| 2008/0289300 A1 | 11/2008 | Gottlieb et al. |
| 2009/0011116 A1 | 1/2009 | Herweck et al. |
| 2009/0036996 A1 | 2/2009 | Roeber |
| 2009/0047414 A1 | 2/2009 | Corbeil et al. |
| 2009/0082864 A1 | 3/2009 | Chen |
| 2009/0092665 A1 | 4/2009 | Mitra et al. |
| 2009/0099651 A1 | 4/2009 | Hakimi-Mehr et al. |
| 2009/0181074 A1 | 7/2009 | Makower et al. |
| 2009/0181937 A1 | 7/2009 | Faucher et al. |
| 2009/0186081 A1 | 7/2009 | Holm et al. |
| 2009/0208552 A1 | 8/2009 | Faucher et al. |
| 2009/0226601 A1 | 9/2009 | Zhong et al. |
| 2009/0240288 A1 | 9/2009 | Guetty |
| 2009/0259235 A1 | 10/2009 | Doucet et al. |
| 2009/0270999 A1 | 10/2009 | Brown |
| 2010/0183697 A1 | 7/2010 | Swanick et al. |
| 2010/0209473 A1 | 8/2010 | Dhont et al. |
| 2010/0233232 A1 | 9/2010 | Swanick et al. |
| 2010/0318108 A1 | 12/2010 | Datta et al. |
| 2011/0028412 A1 | 2/2011 | Cappello et al. |
| 2011/0045050 A1 | 2/2011 | Elbayoumi et al. |
| 2011/0144667 A1 | 6/2011 | Horton et al. |
| 2011/0213302 A1 | 9/2011 | Herweck et al. |
| 2011/0274823 A1 | 11/2011 | Labrecque et al. |
| 2012/0016038 A1 | 1/2012 | Faucher et al. |
| 2012/0213839 A1 | 8/2012 | Faucher et al. |
| 2012/0259348 A1 | 10/2012 | Paul |
| 2012/0315219 A1 | 12/2012 | Labrecque et al. |
| 2013/0041004 A1 | 2/2013 | Drager et al. |
| 2013/0084243 A1 | 4/2013 | Goetsch et al. |
| 2013/0096073 A1 | 4/2013 | Sidelman |

FOREIGN PATENT DOCUMENTS

| | | |
|---|---|---|
| CN | 101448474 A | 6/2009 |
| CN | 102256565 A | 11/2011 |
| DE | 19916086 | 10/1999 |
| DE | 10115740 | 10/2002 |
| EP | 0471566 | 2/1992 |
| EP | 0610731 | 8/1994 |
| EP | 0623354 | 11/1994 |
| EP | 0730864 | 9/1996 |
| EP | 0790822 | 8/1997 |
| EP | 0655222 | 6/1998 |
| EP | 0873133 | 10/1998 |
| EP | 0917561 | 5/1999 |
| EP | 0950386 | 10/1999 |
| EP | 1132058 | 9/2001 |
| EP | 1140243 | 10/2001 |
| EP | 1181943 | 2/2002 |
| EP | 1219265 | 1/2003 |
| EP | 1270024 | 1/2003 |
| EP | 1273314 | 1/2003 |
| EP | 1364628 | 11/2003 |
| EP | 1520795 | 4/2005 |
| EP | 1557183 | 7/2005 |
| EP | 1576970 | 9/2005 |
| EP | 1718347 | 11/2006 |
| EP | 2083875 | 8/2009 |
| EP | 2201965 | 6/2010 |
| EP | 1402906 | 6/2011 |
| EP | 2083875 | 3/2013 |
| GB | 2363572 | 1/2002 |
| JP | 49-50124 | 5/1974 |
| JP | 61-291520 | 12/1986 |
| JP | 1-175864 | 7/1989 |
| JP | 1-503296 | 9/1989 |
| JP | 8-224297 | 9/1996 |
| JP | 2001-10958 | 1/2001 |
| JP | 2006512140 A | 4/2006 |
| JP | 2012505025 A | 3/2012 |
| JP | 2012505030 A | 3/2012 |
| JP | 2013508033 A | 3/2013 |
| KR | 20080025986 | 3/2008 |
| RU | 2125887 | 2/1999 |
| SU | 1297865 | 3/1987 |
| WO | WO 1986/000912 | 7/1984 |
| WO | 87/06463 | 11/1987 |
| WO | WO 1990/001969 | 3/1990 |
| WO | 90/008544 A1 | 8/1990 |
| WO | 93/21912 | 11/1993 |
| WO | 95/17901 | 7/1995 |
| WO | WO 1995/026715 | 10/1995 |
| WO | 96/18417 | 6/1996 |
| WO | 1996/041588 | 12/1996 |
| WO | WO 1997/002042 | 1/1997 |
| WO | WO 1997/009367 | 3/1997 |
| WO | WO 1997/013528 | 4/1997 |
| WO | 98/23228 | 6/1998 |
| WO | WO 1998/030206 | 7/1998 |
| WO | 98/46287 A2 | 10/1998 |
| WO | WO 1998/054275 | 12/1998 |
| WO | 9908544 A1 | 2/1999 |
| WO | WO 1999/025336 | 5/1999 |
| WO | 99/27989 | 6/1999 |
| WO | 99/40874 | 8/1999 |
| WO | 1999/56664 | 11/1999 |
| WO | 00/12147 | 3/2000 |
| WO | 00/40236 | 7/2000 |
| WO | WO 2000/40278 | 7/2000 |
| WO | 00/53212 | 9/2000 |
| WO | WO 2000/62830 | 10/2000 |
| WO | 01/15764 | 3/2001 |

(56) References Cited

FOREIGN PATENT DOCUMENTS

| | | |
|---|---|---|
| WO | WO 2001/024866 | 4/2001 |
| WO | WO 2001/026585 | 4/2001 |
| WO | WO 2001/037808 | 5/2001 |
| WO | 01/45763 | 6/2001 |
| WO | WO 2001/060586 | 8/2001 |
| WO | WO 2001/066036 | 9/2001 |
| WO | WO 2001/076649 | 10/2001 |
| WO | 2001/085060 | 11/2001 |
| WO | 02/22199 | 3/2002 |
| WO | 2002/22047 | 3/2002 |
| WO | WO 2002/049535 | 6/2002 |
| WO | 02/076509 | 10/2002 |
| WO | WO 2002/100455 | 12/2002 |
| WO | WO 2003/000308 | 1/2003 |
| WO | WO 2003/015748 | 2/2003 |
| WO | WO 2003/028622 | 4/2003 |
| WO | 2003/039612 | 5/2003 |
| WO | WO 2003/037397 | 5/2003 |
| WO | WO 2003/037398 | 5/2003 |
| WO | WO 2003/039612 | 5/2003 |
| WO | WO 2003/041756 | 5/2003 |
| WO | WO 03039612 A1 | 5/2003 ............ A61K 31/20 |
| WO | WO 2003/070125 | 8/2003 |
| WO | 2003/073960 | 9/2003 |
| WO | 2003/094787 | 11/2003 |
| WO | WO 2003/092741 | 11/2003 |
| WO | WO 2003/092779 | 11/2003 |
| WO | 2003/105727 | 12/2003 |
| WO | WO 2004/004598 | 1/2004 |
| WO | WO 2004/006976 | 1/2004 |
| WO | WO 2004/006978 | 1/2004 |
| WO | 04/028610 | 4/2004 |
| WO | 2004/028582 | 4/2004 |
| WO | WO 2004/028583 | 4/2004 |
| WO | WO 2004/091684 | 10/2004 |
| WO | 20040101010 A1 | 11/2004 |
| WO | WO 2005/000165 | 1/2005 |
| WO | WO 2005/016400 | 2/2005 |
| WO | WO 2005/053767 | 6/2005 |
| WO | WO 2005/073091 | 8/2005 |
| WO | 2005/082434 A2 | 9/2005 |
| WO | WO 2005/116118 | 12/2005 |
| WO | WO 2006/024488 | 3/2006 |
| WO | WO 2006/036967 | 4/2006 |
| WO | 2006/032812 | 6/2006 |
| WO | WO 2006/102374 | 9/2006 |
| WO | 2007047781 A2 | 4/2007 |
| WO | WO 2007/047028 | 4/2007 |
| WO | 2008/010788 A2 | 1/2008 |
| WO | 2008/016664 A2 | 2/2008 |
| WO | 2008039308 A2 | 4/2008 |
| WO | WO 2008/057328 | 5/2008 |
| WO | 2009091900 A1 | 7/2009 |
| WO | 2010/042134 A1 | 4/2010 |
| WO | 2010/042241 A1 | 4/2010 |
| WO | 2010042134 A1 | 4/2010 |
| WO | 2010042241 A1 | 4/2010 |
| WO | WO 2012/009707 | 1/2012 |

OTHER PUBLICATIONS

Wagner, Karl-Heinz, et al., Effects of tocopherols and their mixtures on the oxidative stability of olive oil and linseed oil under heating, Eur. J. Lipid Sci. Technol., 2000, 624-629, 102.
Non-Final Office Action issued in U.S. Appl. No. 15/817,018, dated Sep. 19, 2018.
Non-Final Office Action issued in U.S. Appl. No. 15/819,304, dated Oct. 5, 2018.
Final Office Action dated May 24, 2019 during the prosecution of related U.S. Appl. No. 15/817,018, 49 pages.
Erhan et al., Vegetable-oil-based printing ink formulation and degradation, Industrial Crops and Products, 1995, 237-246, 3.
Non-Final Office Action issued in U.S. Appl. No. 15/710,514, dated Sep. 17, 2018.
Hawley's Condensed Chemical Dictionary—pp. 425 and 426 (2001), which corresponds to "Exhibit A1."
Stenberg, Cecilia. "Influence of the fatty acid pattern on the drying of linseed oils" (2004).
Champagne et al., Microencapsulation for teh improved delivery of bioactive compounds into foods; Current Opinion in Biotechnology 2007, 18:184-190.
David Schardt, Just the Flax, Nutrition Action Healthletter; Dec. 2005.
Oxford Reference, A Dictionary of Chemistry, 6th edition, John Daintith, 2008, 3 pages.
H. Fineberg et al., Industrial Use of Fish Oils, pp. 222-238, http://spo.nmfs.noaa.gov/Circulars/CIRC278.pdf, downloaded Aug. 3, 2015.
Lewis, Richard J., Sr., Hawley's Condensed Chemical Dictionary, 2001, pp. 308, 309 and 896-898, 14th edision, John Wiley & Sons, Inc., New York.
Webster's II New College Dictionary (1995), 1075, Houghton Mifflin Company, New York, US.
Polymers made from multiple monomers, A Natural Approach to Chemistry, Chapter 8, 241, http://lab-aids.com/assets/uploads/NAC/NAC_student_book/Texas%20Student%20Edition%20253.pdf (downloaded Dec. 3, 2015).
Polymer, Encyclopedia Britannica. Encyclopedia Britannica Online, Encyclopedia Britannica Inc., 105, Web. Dec. 2, 2015, http://www.britannica.com/print/article/468696 (downloaded Dec. 2, 2015).
SepraFilm Adhesion Barrier package insert (Genzyme Biosurgery 2008).
Sannino, Alessandro, et al., Biodegradeable Cellulose-based Hydrogels: Design and Applications, 2 Materials, pp. 353-373, 2009.
Heinz, Thomas, Carboxymethyl Ethers of Cellulose and Starch—A Review, Center of Excellence for Polysaccharide Research, Friedrich Schiller University of Jena (Germany), pp. 13-29, 2005.
Omidian, H. et al., Swelling Agents and Devices in Oral Drug Delivery, J. Drug. Del. Sci. Tech., No. 18, vol. 2, 2008, pp. 83-93.
Kamel, S. et al., Pharmaceutical Significance of Cellulose: A Review, Express Polymer Letters vol. 2, No. 11, 2008, pp. 758-778.
Adel, A. M. et al., Carboxymethylated Cellulose Hydrogel: Sorption Behavior and Characterization, Nature and Science, No. 8, vol. 8, 2010, pp. 244-256.
Bacteria in Water, The USGS Water Science School, http://water.usgs.gov/edu/bacteria.html (downloaded Nov. 9, 2015).
Novotny, L. et al., Fish: a potential source of bacterial pathogens for human beings, Vet. Med.—Czech, 49, 2004, vol. 9, pp. 343-358.
Allergies, Asthma and Allergy Foundation of America (2011), http://www.aafa.org/page/types-of-allergies,aspx (downloaded Oct. 5, 2015).
Sicherer, Scott H., Food Allergies: A Complete Guide for Eating When Your Life Depends on it, 2013, 15, Johns Hopkins University Press, Baltimore, MD, USA.
Omega-3 DHA—The Problem May Be the Quality of Your Fish Oil, Not Your Allergy to Fish, Fatty Acids Hub, http://www.fattyacidshub.com/fatty-acids/omega-3-dha/ (downloaded Nov. 10, 2015).
Soy Allergy, Asthma and Allergy Foundation of America (2005), http://www.aafa.org/display.cfm?id=9&sub=20&cont=522 (downloaded Nov. 10, 2015).
Refined soybean oil not an allergen, say food scientists, Food navigator-usa.com (2005), http://www.foodnavigator-usa.com/content/view/print/127438 (downloaded Nov. 10, 2015).
Yahyaee, R. et al., Waste fish oil biodiesel as a source of renewable fuel in Iran, Renewable and Sustainable Energy Reviews, 2013, pp. 312-319, 17, Elsevier Ltd.
Biological evaluation of medical devices—Part 1: Evaluation and testing, International Standard ISO 109931-1, Aug. 1, 2003, Third Edition, Switzerland.
Mayo Clinic (http://www.mayoclinic.org/drugs-supplements/omega-3-fatty-acids-fish-oil-alpha-linolenic-acids/safety/hrb-20059372?p=1 (downloaded Sep. 28, 2015).
Milk allergy, at http://www.mayoclinic.org/diseases-conditions/milk-allergy/basics/definition/con-20032147?p=1 (downloaded Jul. 29, 2015).

(56) References Cited

OTHER PUBLICATIONS

Soy allergy, at http://www.mayoclinic.org/diseases-conditions/soy-allergy/basics/definition/con-20031370?p=1 (downloaded Jul. 29, 2015).
F.D. Gunstone, Fatty Acid and Lipid Chemistry 72 (1999).
Hawley's Condensed Chemical Dictionary 315, 316, 332, 333, 334, 825 and 826 (2001).
Hutlin, Herbert O. et al., Chemical Composition and Stability of Fish Oil (International Association of Fish Meal Manufacturers Apr. 10, 1991).
F.V.K Young, The Chemical & Physical Properties of Crude Fish Oils for Refiners and Hydrogenators, 18 Fish Oil Bulletin 1-18 (1986).
Karrick, Neva L., Nutritional Value of Fish Oils as Animal Feed, Circular 281 (Fish and Wildlife Service Bureau of Commercial Fisheries 1967), reprinted from M.E. Stansby (ed.), Fish Oils 362-382 (Avi Publishing Company 1967).
Luley et al., Fatty acid composition and degree of peroxidation in fish oil and cod liver oil preparations, Arzneimittelforschung. Dec. 1998, vol. 38, No. 12, pp. 1783-1786.
Drying Oil, http://en.wikipedia.org/wiki/drying_oil (downloaded Jun. 28, 2013).
Szebeni et al., "Complement Activation by Cremophor EL as a Possible Contributor to Hypersensitivity to Paclitaxel: an In Vitro Study", Journal of the National Cancer Institute, 1998, vol. 90, No. 4, pp. 300-306.
Birsan, et al., "The novel calcineurin inhibitor ISA247: a more potent immunosuppressant than cyclosporine in vitro", Transpl. Int., 2005, vol. 17, pp. 767-771.
About.com, "Orthopedics, Synvisc injections," retrieved online at http://orthopedics.about.com/cs/treatment/a/synvisc_2.htm (2005).
Cath Lab Digest, "Olive Oil Emulsion Helps With Problem Heart Arteries", retrieved online at http://www.cathlabdigest.com/displaynews.cfm?newsid=0103073 (2007).
Doctor's Guide to Medical and Other News, "AAOS Meeting: Synvisc Delays Total Knee Replacement in Osteoarthritis Patients", retrieved online at http://www.docguide.com/dg.nsf/PrintPrint/4585EC355198EEF08525670E006B10FF (1999).
Methodist, "Evaluation of Biocompatibility and Antirestenotic Potential of Drug Eluting Stents Employing Polymer-free Highly-Hydrogenated Lipid-Based Stent Coatings in Porcine Coronary Arteries", Transcatheter Cardiovascular Therapeutics (TCT), sponsored by the Cardiovascular Research Foundation®, Oct. 22-27, 2006, Washington Convention Center, Washington, D.C.
Novavax, retrieved online at http://www.novavax.com/go.cfm?do=Page.View&pid=3 (2006).
Orthovisc, "New Treatment Option is Potential Alternative to OTC Pain Medications for Osteoarthritis of the Knee" retrieved online at http://www.jnj.com/innovations/new_features/ORTHOVISC.htm:iessionid=33N2RBQDV0DZKCQPCCEGU3AKB2IIWTT1 (2006).
Orthovisc, "What is Orthovisc®?" retrieved online at http://www.orthovisc.com/xhtmlbgdisplay.jhtml?itemname=about_orthovisc (2005).
Orthovisc, "Your Knees and Osteoarthritis", retrieved online at http://www.orthovisc.com/xhtmlbgdisplay.jhtml?itemname=understanding_knee_oa (2005).
Orthovisc, "What to expect from your treatment," retrieved online at http://www.orthovisc.com/xhtmlbgdisplay.jhtml?itemname=what_to_expect (2007).
Orthovisc, "Tools and Resources for Managing Your Osteoarthritis", retrieved online at http://www.orthovisc.com/xhtmlbgdisplay.jhtml?itemname=patient_resources (2007).
Pohibinska, A., et al., "Time to reconsider saline as the ideal rinsing solution during abdominal surgery", The American Journal of Surgery, vol. 192, pp. 281-222 (2007).
Singh, Alok, et al., "Facilitated Stent Delivery Using Applied Topical Lubrication", Catherization and Cardiovascular Interventions, vol. 69, pp. 218-222 (2007).
Urakaze, Masaharu et al., "Infusion of fish oil emulsion: effects on platelet aggregation and fatty acid composition in phospholipids of plasma, platelets and red blood cell membranes in rabbits", Am. J. Clin. Nutr., vol. 46, pp. 936-940 (! 987).
Hortolam, Juliane G., et al., "Connective tissue diseases following silicone breast implantation: where do we stand?", Clinics, 2013, vol. 3, p. 281.
Lidar, M. et al., "Silicone and sclerodema revisited", Lupus, 2012, vol. 21, pp. 121-127.
Swanson, Danielle, et al., Omega-3 Fatty Acids EPA and DHA: Health Benefits Throughout Life, 3 Advances in Nutrition 1-7 (American Society for Nutrition 2012).
Triglycerides, https://www.lipid.org/sites/default/files/triglycerides.pdf (downloaded Sep. 24, 2015).
Fish Oil Triglycerides vs. Ethyl Esters: A Comparative Review of Absorption, Stability and Safety Concerns (Ascenta Health Ltd. 2010 at http://www.ascentaprofessional.com/science/articles/fish-oil-triglycerides-vs-ethyl-esters (downloaded Sep. 24, 2015).
Fats & Oils (2008) at http://scifun.chem.wisc.edu/chemweek/pdf/fats&oils.pdf (downloaded Sep. 24, 2015).
"Lead", Article by Centers for Disease Control and Prevention (CDC), Nov. 2009, 2 pages.
"Cure" in Academic Press Dictionary of Science and Technology, 1992.
Wicks et al. Organic Coatings:Science and Technology 1999 New York:Wiley Interscience p. 258-267.
Mills et al. Oils and Fats. "The Organic Chemistry of Museum Objects" London:Buttersworth and Co. 1987, p. 26-40.
Erhardt Paints Based on Drying Oil Media. Painted Wood: History & Conservation. Ed. Berland Singapore: The J. Paul Getty Trust 1998. p. 17-32.
Wexler et al. Chemical Reviews 1964 64(6):591-611.
Polymer—The Chambers 21st Century Dictionary M. Robinson and G. Davidson (Eds.), London, United Kingdom: Chambers Harrap. Retrieved from http://search.credoreference.com/content/entry/chambdict!polymer/O.
Polymer—Academic Press Dictionary of Science and TechnologyC. Morris (Ed.), Academic Press Dictionary of Science and Technology. Oxford, United Kingdom: Elsevier Science & Technology. Retrieved from http://search.credoreference.com/content/entry/apdst!polymer/O.
Falagas et al. European Society of Clinical Microbiology and Infection Diseases 2005 11:3-8.
Bimbo (Inform 1998 9(5):473-483.
Wikipedia, Sunflower oil, https://en.wikipedia.org/wiki/Sunflower_oil, accessed Jul. 23, 2015 in related U.S. Appl. No. 14/252,671, pp. 1-7.
Esoteric Oils, Peppermint essential oil information, http://www.essentialoils.co.za/essential-oils/peppermint.htm, accessed Jul. 23, 2015 in related U.S. Appl. No. 14/252,671, pp. 1-7.
Orthomolecular, Fish Oil, Jun. 29, 2004, http://orthomolecular.org/nutrients/fishoil.html, accessed Jul. 22, 2015 in related U.S. Appl. No. 14/252,671, p. 1.
Ackman, R.G., "Fish Oils", *Bailey's Industrial Oil and Fat Products*, 6$^{th}$ Edition, 279-317 (2005).
Ahuja et al. Journal of Indian Pediatric Surgery 2002 7:15-20.
Andes, et al. "Antiproliferative Strategies for the Treatment of Vascular Proliferative Disease", *Current Vascular Pharmacology*, 1)1): 85-98 (2003).
A paper entitled "Evaluation of the Biocompatibility and Drug Delivery Capabilities of Biological Oil Based Stent Coatings" by Shengqio Li of the Katholieke Universiteit Leuven.
Autosuture, "ParietexTM Composite OS Series Mesh," retrieved online at http://www.autosuture.com/AutoSuture/pagebuilder.aspx?topicID=135734&breadcrumbs=135601:0 (2007).
Binder et al., "Chromatographic Analysis of Seed Oils. Fatty Acid Composition of Castor Oil," The Journal of the American Oil Chemists' Society, vol. 39:513-517 (1962).
Camurus, "In our endeavors to create the unique, we start with the best. Your product."
CECW-EE, "Ch. 4: Coating Types and Characteristics," Engineering and Design—Painting: New Construction and Maintenance, pp. 4-1 to 4-24 (1995).

(56) References Cited

OTHER PUBLICATIONS

Crivello et al., "Epoxidized triglycerides as renewable monomers in photoinitiated cationic polymerization," Chem. Mater, 1992:692-699.
De Scheerder, Ivan K., et al. "Biocompatibility of polymer-coated oversized metallic stents implanted in normal porcine coronary arteries," Atherosclerosis, vol. 114:105-114.
Drummond, Calum J., et al., "Surfactant self-assembly objects as novel drug delivery vehicles," Current Opinion in Colliod & Interface Science, vol. 4:449-456 (2000).
Encylopedia Britannica Online, "Surface Coating," available online at http://www.britannica.com/Ebchecked/topic/575029/surface-coating>, date accessed Jun. 17, 2011.
Engstrom, Sven, "Drug Delivery from Cubic and Other Lipid-water Phases," Lipid Technology, vol. 2(2):42-45 (1990).
Guler, et al. "Some empirical equations for oxopolymerization of linseed oil," Progress in Organic Coatings, vol. 51:365-371 (2004).
Hwang, Chao-Wei, et al, "Physiological Transport Forces Govern Drug Distribution for Stent-Based Delivery," Circulation, vol. 104:600-605 (2001).
Jonasson, Lena et al., "Cyclosporon A inhibits smooth muscle proliferation in the vascular response to injury," Proc. Natl. Acad. Sci. USA, vol. 85: 2303-2306 (1988).
Jorge, N., "Grasas y Aceites", 48(1): 17-24, (1997).
Lipids, Chapter 19, pp. 1-12 (2002).
Mallegol, et al., "Drier Influence on the Curing of Linseed Oil," Progress in Organic Coatings 39:107-113 (2000).
Morse, Richard "Molecular Distillation of Polymerized Drying Oils," Industrial and Engineering Chemisry 33:1039-1043 (1941).
Oberhoff, Martin, et al, "Local and Systemic Delivery of Low Molecular Weight Heparin Following PTCA: Acute Results and 6-Month Follow-Up of the Initial Clinical Experience With the Porous Balloon (Pilot-Study)," Catheterization and Cardiovascular Diagnosis, vol. 44:267-274 (1998).
Ogunniyi, D.S., "Castor oil: A vital industrial raw material," Biosource Technology, vol. 97:1086-1091 (2006).
Polymerization Merriam-Webster Online Dictionary, retrieved from <www.merriam-webster.com> on Dec. 13, 2009; Merriam-Webster's Inc. 2009; pp. 1.
Redman, L.V. et al., "The drying rate of raw paint oils—a comparison," The Journal of Industrial and Engineering Chemistry, vol. 5: 630-636 (1913).
Rutkow, Ira M. et al., "'Tension-free' inguinal herniorrhaphy: A preliminary report on the 'mesh plug' technique," Surgery, vol. 114:3-8 (1993).
Salu, Koen J., et al, "Addition of cytochalasin D to a biocompatible oil stent coating inhibits intimal hyperplasia in a porcine coronary model," Coronary Artery Disease, vol. 14(8):545-555 (2003).
Scheller, Bruno, et al, "Addition of Paclitaxel to Contrast Media Prevents Restenosis After Coronary Stent Implantation," Journal of the American College of Cardiology, vol. 42(8):1415-1420 (2003).
Shahidi, Fereidoon ed.; "Bailey's Industrial Oil and Fats Products" 2005; John Wiley and Sons; vol. 5, Edible Oil and Fat Products: Processing Technologies, pp. 1-15.
Timar-Balizsy et al., "Chemical Principals of Textile Conservation," Oxford: Elsevier Science Ltd., 1998:117-119.
Van der Giessen, Willem J., et al, "Marked Inflammatory Sequelae to Implantation of Biodegradable and Nonbiodegradable Polymers in Porcine Coronary Arteries," Circulation, vol. 94:1690-1697 (1996).
Websters Dictionary Online, Accessed on Feb. 13, 2009, entry for "polymer" p. 1 of 1.
Wikipedia, "Sirolimus," pp. 1-13, available online at http://en.wikipedia.org/wiki/Sirolimus, date accessed May 11, 2011.
Winter, et al., "Physical and Chemical Gelation" *Encyclopedia of Materials—Science and Technology*, vols. 1-11: 6691-6699 (2001).
Mallegol, "Long-Term Behavior of Oil-Based Varnishes and Paints Photo-and Thermooxidation of Cured Linseed Oil", *Journal of the American Oil Chemists' Society*, 77:257-263 (2000).
Uchida, et al., "Swelling Process and Order-Disorder Transition of Hydrogel Containing Hydrophobic Ionizable Groups", *Macromolecules*, 28, 4583-4586 (1995).
Gutfinger, et al., "Polyphenols in Olive Oils", *Journal of the American Oil Chemists Society*, 58(11): 966-968 (1981).
Portilla, et al., "Prevention of Peritoneal Adhesions by Intraperitoneal Administration of Vitamin E: An Experimental Study in Rats", *Diseases of the Colon and Rectum*, 47; 2157-2161 (2005).
Sano, et al., "A controlled Trial of Selegiline, Alpha-Tocopherol, or Both as Treatment for Alzheimer's Disease", *The New England Journal of Medicine*, 336; 1216-1222 (1997).
International Search Report for International Application PCT/US05/034601, dated Apr. 10, 2006.
International Search Report for International Application PCT/US05/034610, dated Mar. 16, 2006.
International Search Report for International Application PCT/US05/034614, dated Aug. 29, 2006.
International Search Report for International Application PCT/US05/034615, dated May 16, 2006.
International Search Report for International Application PCT/US05/034678, dated Aug. 28, 2006.
International Search Report for International Application PCT/US05/034681, dated Jul. 26, 2006.
International Search Report for International Application PCT/US05/034682, dated Jul. 20, 2006.
International Search Report for International Application PCT/US05/034836, dated Jul. 6, 2006.
International Search Report for International Application PCT/US06/037184, dated Feb. 22, 2007.
International Preliminary Report on Patentability for International Application PCT/US06/040753, dated Oct. 3, 2008.
International Search Report for International Application PCT/US06/040753, dated Sep. 24, 2007.
International Search Report for International Application PCT/US07/019978, dated May 7, 2009.
International Search Report for International Application PCT/US07/022860, dated Apr. 22, 2009.
International Search Report for International Application PCT/US07/022944, dated Apr. 8, 2009.
International Search Report for International Application PCT/US08/000565, dated May 4, 2009.
International Preliminary Examination Report for International Application PCT/US08/071547, dated Aug. 26, 2010.
International Search Report for International Application PCT/US08/071547, dated Oct. 22, 2008.
International Preliminary Report on Patentability for International Application PCT/US08/071565, dated Aug. 27, 2009.
International Search Report for International Application PCT/US08/071565, dated Nov. 10, 2008.
International Search Report for International Application PCT/US08/085386, dated Feb. 4, 2009.
International Search Report for International Application PCT/US09/037364, dated Aug. 27, 2009.
International Search Report for International Application PCT/US10/026521, dated Jun. 23, 2010.
International Search Report for International Application PCT/US10/052899, dated Jan. 10, 2011.
Supplementary European Search Report for Application No. EP 05 80 2894, dated Jul. 27, 2011.
Supplementary European Search Report in Application No. 05 800 844, dated Aug. 19, 2011.
Supplementary European Search Report in Application No. EP 05 80 4291, dated Jul. 26, 2011.
Supplementary European Search Report in Application No. EP 05 85 8430, dated Aug. 18, 2011.
International Search Report for International Application No. PCT/US05/34941, dated May 4, 2006.
Supplementary European Search Report for Application No. EP 08877338.7, dated Aug. 16, 2012.
Supplementary European Search Report for Application No. EP09819594.4, dated Aug. 14, 2012.
International Search Report for PCT/US2011/44292, dated Dec. 6, 2011.

(56) References Cited

OTHER PUBLICATIONS

Supplementary European Search Report for Application No. EP 12004057, dated Apr. 10, 2013.
International Search Report for International Application PCT/US2013/044653, dated Sep. 4, 2013.
Supplementary European Search Report for Application No. EP 10825447, dated Mar. 31, 2014.
Non-final Office Action for U.S. Appl. No. 11/236,908 (listed on SB/08 as US 2006/0067974), dated Mar. 25, 2006.
Final Office Action for U.S. Appl. No. 11/236,908 (listed on SB/08 as US 2006/0067974), dated May 17, 2011.
Non-final Office Action for U.S. Appl. No. 11/236,908 (listed on SB/08 as US 2006/0067974), dated Aug. 24, 2009.
Non-final Office Action for U.S. Appl. No. 11/236,977 (listed on SB/08 as US 2006/0088596), dated Aug. 3, 2009.
Final Office Action for U.S. Appl. No. 11/237,263 (listed on SB/08 as US 2006/0110457), dated Jul. 7, 2010.
Non-final Office Action for U.S. Appl. No. 11/237,263 (listed on SB/08 as US 2006/0110457), dated Oct. 7, 2009.
Final Office Action for U.S. Appl. No. 11/237,264 (listed on SB/08 as US 2006/0067983), dated Jun. 2, 2010.
Non-final Office Action for U.S. Appl. No. 11/237,264 (listed on SB/08 as US 2006/0067983), dated Oct. 5, 2009.
Final Office Action for U.S. Appl. No. 11/701,799 (listed on SB/08 as US 2008/0109017), dated Nov. 23, 2010.
Non-final Office Action for U.S. Appl. No. 11/237,420 (listed on SB/08 as US 2006/0078586), dated Mar. 5, 2009.
Final Office Action for U.S. Appl. No. 11/237,420 (listed on SB/08 as US 2006/0078586), dated Nov. 4, 2009.
Non-final Office Action for U.S. Appl. No. 11/237,420 (listed on SB/08 as US 2006/0078586), dated Dec. 6, 2010.
Non-final Office Action for U.S. Appl. No. 11/238,532 (listed on SB/08 as US 2006/0067976), dated Mar. 30, 2009.
Final Office Action for U.S. Appl. No. 11/238,532 (listed on SB/08 as US 2006/0067976), dated Sep. 9, 2009.
Final Office Action for U.S. Appl. No. 11/238,554 (listed on SB/08 as US 2006/0121081), dated May 12, 2010.
Non-final Office Action for U.S. Appl. No. 11/238,554 (listed on SB/08 as US 2006/0121081), dated Oct. 9, 2009.
Final Office Action for U.S. Appl. No. 11/238,554 (listed on SB/08 as US 2006/0121081), dated May 1, 2009.
Non-final Office Action for U.S. Appl. No. 11/238,554 (listed on SB/08 as US 2006/0121081), dated Jul. 25, 2008.
Non-final Office Action for U.S. Appl. No. 11/238,564 (listed on SB/08 as US 2006/0083768), dated Apr. 16, 2008.
Final Office Action for U.S. Appl. No. 11/238,564 (listed on SB/08 as US 2006/0083768), dated Aug. 6, 2009.
Non-final Office Action for U.S. Appl. No. 11/239,555 (listed on SB/08 as US 2006/0067977), dated Mar. 30, 2009.
Non-final Office Action for U.S. Appl. No. 11/525,328 (listed on SB/08 as US 2007/0084144), dated Apr. 30, 2007.
Non-final Office Action for U.S. Appl. No. 11/525,390 (listed on SB/08 as US 2007/0071798), dated Jul. 14, 2010.
Final Office Action for U.S. Appl. No. 11/525,390 (listed on SB/08 as US 2007/0071798), dated Feb. 21, 2011.
Final Office Action for U.S. Appl. No. 11/582,135 (listed on SB/08 as US 2007/0202149), dated May 12, 2011.
Non-final Office Action for U.S. Appl. No. 11/582,135 (listed on SB/08 as US 2007/0202149), dated Nov. 9, 2010.
Non-final Office Action for U.S. Appl. No. 11/582,135 (listed on SB/08 as US 2007/0202149), dated Jan. 6, 2010.
Non-final Office Action for U.S. Appl. No. 11/582,135 (listed on SB/08 as US 2007/0202149), dated May 12, 2009.
Non-final Office Action for U.S. Appl. No. 11/701,799 (listed on SB/08 as US 2008/0109017), dated Apr. 12, 2010.
Non-final Office Action for U.S. Appl. No. 11/978,840 (listed on SB/08 as US 2008/0118550), dated Dec. 3, 2010.
Non-final Office Action for U.S. Appl. No. 11/980,155 (listed on SB/08 as US 2008/0113001), dated Mar. 24, 2011.
Non-final Office Action for U.S. Appl. No. 12/075,223 (listed on SB/08 as US 2008/0206305), dated Dec. 8, 2010.
Non-final Office Action for U.S. Appl. No. 12/325,546 (listed on SB/08 as US 2009/0181937), dated Feb. 25, 2010.
Final Office Action for U.S. Appl. No. 12/325,546 (listed on SB/08 as US 2009/0181937), dated Aug. 31, 2010.
Non-final Office Action for U.S. Appl. No. 12/364,763 (listed on SB/08 as US 2009/0208552), dated Dec. 11, 2009.
Final Office Action for U.S. Appl. No. 12/364,763 (listed on SB/08 as US 2009/0208552), dated Sep. 21, 2010.
Interview summary for U.S. Appl. No. 11/236,908 (listed on SB/08 as US 2006/0067974) dated May 5, 2009.
Interview summary for U.S. Appl. No. 11/237,420 (listed on SB/08 as US 2006/0078586) dated May 5, 2009.
Interview summary for U.S. Appl. No. 11/582,135 (listed on SB/08 as US 2007/0202149) dated Dec. 7, 2010.
Interview summary for U.S. Appl. No. 12/325,546 (listed on SB/08 as US 2009/0181937) dated Dec. 2, 2010.
Interview summary for U.S. Appl. No. 12/364,763 (listed on SB/08 as US 2009/0208552) dated Dec. 2, 2010.
Final Office Action for U.S. Appl. No. 11/237,420 (listed on SB/08 as US 2006/0078586), dated Jul. 13, 2011.
Final Office Action for U.S. Appl. No. 11/978,840 (listed on SB/08 as US 2008/0118550), dated Jun. 22, 2011.
Final Office Action for U.S. Appl. No. 12/075,223 (listed on SB/08 as US 2008/0206305), dated Aug. 11, 2011.
Non-final Office Action for U.S. Appl. No. 11/525,390 (listed on SB/08 as US 2007/0071798), dated Jul. 11, 2011.
Non-Final Office Action for U.S. Appl. No. 11/701,799 (listed on SB/08 as US 2008/0109017), dated Aug. 17, 2011.
Final Office Action for U.S. Appl. No. 11/980,155 (listed on SB/08 as US-2008-0113001), dated Oct. 21, 2011.
Non-Final Office Action for U.S. Appl. No. 11/236,908 (listed on SB/08 as US-2006-0067974), dated Dec. 2, 2011.
Non-Final Office Action for U.S. Appl. No. 12/182,261 (listed on SB/08 as US 2009-0047414), dated Dec. 21, 2011.
Notice of Allowance for U.S. Appl. No. 11/582,135 (listed on SB/08 as US 2007-0202149), dated Jan. 9, 2012.
Non-Final Office Action for U.S. Appl. No. 12/182,165 (listed on SB/08 as US 2009-0011116), dated Jan. 5, 2012.
Final Office Action for U.S. Appl. No. 11/701,799 (listed on SB/08 as US 2008/0109017), dated Feb. 13, 2012.
Non-Final Office Action for U.S. Appl. No. 12/581,582 (listed on SB/08 as US 2010-0183697), dated Mar. 14, 2012.
Final Office Action for U.S. Appl. No. 12/182,165 (listed on SB/08 as US 2009-0011116), dated Apr. 6, 2012.
Final Office Action for U.S. Appl. No. 12/182,261 (listed on SB-08 as US 2009/0047414) dated Apr. 30, 2012.
Notice of Allowance for U.S. Appl. No. 11/236,908 (listed on SB/08 as US-2006-0067974), dated May 11, 2012.
Notice of Allowance for U.S. Appl. No. 12/182,261 (listed on SB/08 as US US-2009-0047414), dated Jul. 23, 2012.
Advisory Action for U.S. Appl. No. 12/401,243 (listed on SB/08 as US 2010-0233232), dated Aug. 27, 2012.
Final Office Action for U.S. Appl. No. 12/581,582 (listed on SB-08 as US 2010/0183697) dated Aug. 29, 2012.
Notice of Allowance for U.S. Appl. No. 11/525,390 (listed on SB/08 as US-2007/0071798), dated Oct. 4, 2012.
Final Office Action for U.S. Appl. No. 11/236,943 (listed on SB/08 as US 2006/0067975), dated Dec. 23, 2009.
Non-Final Office Action for U.S. Appl. No. 11/236,943 (listed on SB/08 as US 2006/0067975), dated Mar. 5, 2009.
Advisory Action for U.S. Appl. No. 12/581,582 (listed on SB/08 as US 2010-0183697), dated Nov. 14, 2012.
Non-Final Office Action for U.S. Appl. No. 13/404,487 (listed on SB/08 as 2012-0213839), dated Dec. 20, 2012.
Notice of Allowance for U.S. Appl. No. 11/525,390 (listed on SB/08 as US-2007/0071798), dated Nov. 20, 2012.
Advisory Action for U.S. Appl. No. 12/581,582 (listed on SB-08 as U.S. Publication No. 2010-0183697), dated Nov. 14, 2012.
Notice of Allowance for U.S. Appl. No. 11/525,390 (listed on SB-08 as U.S. Publication No. US-2007-0071798), dated Nov. 20, 2012.

(56) References Cited

OTHER PUBLICATIONS

Non-Final Office Action for U.S. Appl. No. 13/404,487 (listed on SB-08 as US 2012-0213839), dated Dec. 20, 2012.
Non-Final Office Action for U.S. Appl. No. 13/184,512 (listed on SB-08 as 2012-0016038), dated Jan. 31, 2013.
Non-Final Office Action for U.S. Appl. No. 11/978,840 (listed on SB-08 as U.S. No. US-2008-0118550), dated Feb. 19, 2013.
Non-Final Office Action for U.S. Appl. No. 13/682,991 (listed on SB-08 as U.S. No. US-2013-0074452), dated Mar. 18, 2013.
Notice of Allowance for U.S. Appl. No. 13/404,487 (listed on SB-08 as U.S. No. US- 2012-0213839), dated Apr. 2, 2013.
Non-Final Office Action for U.S. Appl. No. 11/236,943 (listed on SB-08 as U.S. No. US-2006-0067975), dated Apr. 22, 2013.
Final Office Action for U.S. Appl. No. 13/184,512 (listed on SB-08 as U.S. No. U.S. 2012-0016038), dated Jun. 25, 2013.
Non-Final Office Action for U.S. Appl. No. 11/237,264 (listed on SB-08 as U.S. No. US-2006-0067983), dated Jul. 3, 2013.
Non-Final Office Action for U.S. Appl. No. 13/593,656 (listed on SB-08 as U.S. No. US-2012-03115219), dated Jul. 15, 2013.
Notice of Allowance for U.S. Appl. No. 13/682,991 (listed on SB-08 as U.S. Publication No. US 2013-0074452), dated Aug. 1, 2013.
Notice of Allowance for U.S. Appl. No. 11/978,840 (listed on SB-08 as U.S. Publication No. US-2008-0118550), dated Aug. 6, 2013.
Final Office Action for U.S. Appl. No. 11/236,943 (listed on SB-08 as U.S. Publication No. US- 2006-0067975), dated Dec. 4, 2013.
Final Office Action for U.S. Appl. No. 11/237,264 (listed on SB-08 as U.S. Publication No. US-2006-0067983), dated Dec. 17, 2013.
Notice of Allowance for U.S. Appl. No. 13/593,656 (listed on SB-08 as U.S. Publication 2012-03115219), dated Jan. 24, 2014.
Notice of Allowance for U.S. Appl. No. 11/237,264 (listed on SB-08 as U.S. Publication No. US-2006-0067983), dated Mar. 27, 2014.
Notice of Allowance for U.S. Appl. No. 11/237,263 (listed on SB-08 as U.S. Publication No. US-2006-0110457), dated Mar. 27, 2014.
Non Final Office Action for U.S. Appl. No. 12/325,546 (listed on SB-08 as U.S. Publication No. US-2009-0181937), dated Apr. 22, 2014.
Non Final Office Action for U.S. Appl. No. 12/364,763 (listed on SB-08 as U.S. Publication No. US-2009-0208552), dated Apr. 23, 2014.
Non Final Office Action for U.S. Appl. No. 12/401,243 (listed on SB/08 as US 2010-0233232), dated May 8, 2014.
Non Final Office Action for U.S. Appl. No. 12/581,582 (listed on SB-08 as U.S. Publication 2010-0183697), dated May 29, 2014.
Non-Final Office Action for U.S. Appl. No. 13/943,489, dated Jul. 1, 2014.
Final Office Action for U.S. Appl. No. 11/980,155, dated Jul. 21, 2014.
Final Office Action for U.S. Appl. No. 11/237,420, dated Jul. 22, 2014.
Non-Final Office Action for U.S. Appl. No. 11/701,799, dated Jul. 22, 2014.
Final Office Action for U.S. Appl. No. 12/075,223, dated Jul. 22, 2014.
Non-Final Office Action for U.S. Appl. No. 13/843,068, dated Sep. 29, 2014.
Notice of Allowance for U.S. Appl. No. 11/236,943 (listed on SB-08 as U.S. Publication No. US-2006-0067975), dated Oct. 6, 2014.
Non-Final Office Action for U.S. Appl. No. 13/184,512, dated Oct. 10, 2014.
Non-Final Office Action for U.S. Appl. No. 12/075,223, dated Oct. 29, 2014.
Non-Final Office Action for U.S. Appl. No. 11/980,155, dated Nov. 7, 2014.
Notice of Allowance for U.S. Appl. No. 12/364,763 (listed on SB-08 as U.S. Publication No. US-2009-0208552), dated Dec. 5, 2014.
Notice of Allowance for U.S. Appl. No. 12/325,546 (listed on SB-08 as U.S. Publication No. US-2009-0181937), dated Dec. 8, 2014.
Final Office Action for U.S. Appl. No. 12/581,582, dated Jan. 8, 2015.
Final Office Action for U.S. Appl. No. 12/401,243, dated Jan. 16, 2015.
Non-Final Office Action for U.S. Appl. No. 11/237,420, dated Jan. 21, 2015.
Notice of Allowance for U.S. Appl. No. 13/943,489, dated Jan. 29, 2015.
Final Office Action for U.S. Appl. No. 11/701,799, dated Mar. 12, 2015.
Final Office Action for U.S. Appl. No. 13/843,068, dated Apr. 23, 2015.
Final Office Action for U.S. Appl. No. 13/184,512, dated Apr. 28, 2015.
Senzyme Corporation, 510(k) Notification, Section 10: 510(k) Summary, Dec. 21, 1999, 11 pages.
Deeken, Corey R., et al., A review of the composition, characteristics, and effectiveness of barrier mesh prostheses utilized for laparoscopic ventral hernia repair, Surg Endosc, 2011, 10 pages.
"What are Omega-9 Fats?", Paleo Leap, LLC, printed from http://paleoleap.com/omega-9-fats on Sep. 14, 2016, 5 pages.
Kumar, Ashavani, et al., "Silver-nanoparticle-embedded antimicrobial paints based on vegetable oil", Nature Materials, vol. 7, Mar. 2008, pp. 236-241.
Shriner, Ralph L., et al., "The Systematic Identification of Organic Compounds—A laboratory manual", pp. 284 and 285, 6th ed. (John Wiley & Sons—1980).
Olive Oil Reference Book (PerkinElmer, Inc. 2012), pp. 1-48.
Standard for Olive Oils and Olive Pomace Oils, Codex Stan 33/1981 (World Health Organization 2013), pp. 1-9.
Wang, Wei, et al., "Directing Oleate Stabilized Nanosized Silver Colloids into Organic Phases", Langmuir, vol. 14, No. 3, (1998), pp. 602-610.
Cheong et al., "Peritoneal healing and adhesion formation/reformation", Human Reproduction Update. 7(6):556-566 (2001).
Carbonell et al., "The susceptibility of prosthetic biomaterials to infection", Surgical Endoscopy. 19:430-435(2005).
Kuijer et al., "Assessing infection risk in implanted tissue-engineered devices", Biomaterials. 28:5148-5154 (2007).
Arciola et al., "Strong biofilm production, antibiotic multi-resistance and high gelE expression in epidemic clones of Enterococcus faecalis from orthopaedic implant infections", Biomaterials. 29:580-586(2008) (abstract).
Zheng et al., "Fatty acid synthesis is a target for antibacterial activity of unsaturated fatty acids", Febs Letters, Elsevier, Amsterdam, NL, vol. 579, No. 23, Sep. 26, 2005, pp. 5157-5162.
Lee, Ji-Young et al., "Antimicrobial Synergistic Effect of Linolenic Acid and Monoglyceride against Bacillus cereus and Staphylococcus aureus", Journal of Agricultural and Food Chemistry, vol. 50, No. 7, Mar. 1, 2002, pp. 2193-2199.
Larsen, D. et al.., "Effect of cooking method on the fatty acid profile of New Zealand King Salmon (Oncorhynchus tshawytscha)" Food Chemistry 119 (2010) 785-790 (Year: 2010).
Steiner, M. et al. " Effect of Local Processing Methods (Cooking, Frying and Smoking) on Three Fish Species from Ghana: Part I. Proximate Composition, Fatty Acids, Minerals, Trace Elements and Vitamins" Food Chemistry 40 (1991) 309-321 (Year: 1991).
Gruger, Jr. E.H. Fatty Acid Composition. NMFS Scientific Publications by BOFC Fisheries. (http://spo.nmfs.noaa.gov/Circulars/CIRC276.pdf) 1967, pp. 1-30 (Year: 1967).
"Scientific Opinion on Fish Oil for Human consumption. Food Hygiene, including Rancidity", EFSA Journal—pp. 1-48, vol. 8, (2010).
"Gas Chromatography Theory"—updated Apr. 1, 2016—http://www.chem.ucia.eduPY07Ebacher/Genera1/30BL/gc,/theory.html.
Lehotay, Steven J., et al., "Application of Gas Chromatography in Food Analysis", Trends in Analytical Chemistry—pp. 686-697, vol. 21, (2002).
Edible Oils. (http://www.chempro.inffallyacid.htm) accessed Apr. 14, 2014.
Malayoglu et al. "Dietary vitamin E (a-tocopheryl acetate) and organic selenium supplementation: performance and antioxidant status of broilers fed n-3 Pufa-enriched feeds" South African Journal of Animal Science 2009, 39 (4), pgs. 274-285 (Year: 2009).

(56) References Cited

OTHER PUBLICATIONS

Therapeutic definition (http://www.thefreedictionary.comitherapeutic) accessed Apr. 29, 2016.
Viscosity (http://www.vp-scientific.com/pdfs/www.liquidcontrol.com_eToolbox_viscosity.pdf) accessed Jan. 6, 2017, pp. 1-4.
Bechert et al., "A New Method for Screening Anti-Infective Biomaterials", Nature Medicine, 6(8): 1053-1056 (2000).
Douglas, Kyle, et al., Zero-Order Controlled-Release Kinetics Through Polymer Matrices, available at http://www.drew.edu/wp-content/uploads/sites/99/Team5.pdf (downloaded Dec. 21, 2016).
Multanen, M., et al., Bacterial adherence to silver nitrate coated poly-L-lactic acid urological stents in vitro, Urol Res., Oct. 2000, 327-31, 5. (Abstract).
Babaev, Vladimir R., et al., Macrophage Lipoprotein Lipase Promotes Foam Cell Formation and Atherosclerosis in Vivo, 103 The Journal of Clinical Investigation, 1999, 1697-1705.
Moreno-Egea, "Laparoscopic repair of Ventral and Incisional Hernias Using a new Composite Mesh (Parletex)," Surgical Laparoscopy, Endoscopy & Percutaneous Techniques, 2001, vol. 11, No. 2, pp. 103-106.
Nagao et al., "Conjugated Fatty Acids in Food and Their Health Benefits," 2005, The Society for Biotechnology, Japan, Journal of Bioscience and Bioengineering, vol. 100, No. 2, pp. 152-157.
Nair et al. Journal of Dairy Science 2005 88:3488-3495.
Nakatsuji et al. Journal of Investigative Dermatology 2009 129(10): 2480-2488.
Non-Final OA for U.S. Appl. No. 11/140,811 dated Sep. 15, 2008.
Non-Final OA for U.S. Appl. No. 12/767,289 dated Aug. 19, 2011.
Non-Final OA for U.S. Appl. No. 12/767,289 dated Mar. 15, 2012.
Non-Final Office Action for U.S. Appl. No. 12/401,243 (listed on SB/08) as US 2010/0233232, dated Jan. 5, 2012.
Non-Final Office Action for U.S. Appl. No. 13/184,512 (listed on SB-08 as US 2012-0016038), dated Jan. 31, 2013.
Non-Final Office Action for U.S. Appl. No. 11/711,389, dated Dec. 17, 2010.
Non-Final Office Action for U.S. Appl. No. 12/401,228, dated Nov. 12, 2010.
Non-Final Office Action for U.S. Appl. No. 11/582,135 (listed on SB/08 as US-2007-0202149), dated Oct. 14, 2011.
Non-Final Office Action of U.S. Appl. No. 12/182,165, dated Jun. 24, 2013.
Non-Final Office Action of U.S. Appl. No. 13/185,135, dated Jan. 25, 2011.
Notice of Allowance for U.S. Appl. No. 11/525,390 (listed on SB/08 as US-2007/0071798), dated Nov. 30, 2012.
Notice of Allowance of U.S. Appl. No. 11/238,554, dated Apr. 28, 2011.
O'Neil, Maryadelle J. et al., The Merck Index—An Encyclopedia of Chemicals, Drugs, and Biologicals, 14th ed., 2006, entries for "Calcium Carbonite", "Cyclosporins", "Prussian Blue", and "Rapamycin", pp. 1-12.
Pandey et al. Tuberculosis 2005 85:227-234.
Pearlman, Daniel D. & Paul R., "Guide to Rapid Revision," 3rd ed., 1982, Bobbs-Merrill Educational Publishing, pp. 25-27.
Pilz and Marz 2008, Free fatty acids as a cardiovascular risk factor. Clin Chem Lab Med, vol. 46, No. 4, pp. 429-434.
Preparation of Methyl Esters of Fatty Acids, AOCS Official Method Ce 2-66 (2009), pp. 1-2.
Rietjens et al., "The pro-oxidant chemistry of the natural antioxidants vitamin C, vitamin E, carotenoids, and flavonoids," Environmental Toxicology and Pharmacology, 2002, vol. 11, pp. 321-333.
Salvolainen et al. International Journal of Pharmaceutics 2002 244:151-161.
Schwartz et al., "Restenosis and the Proportional Neointimal Response to Coronary Artery Injury: Results in a Porcine Model," J. Am. Coll. Cardiol., 1992, vol. 19, pp. 267-274.
Shakhashiri, Chemical of the week Fats and Oils, at www.scifun.org (last revised Jan. 30, 2008) 2 pages.
"Sharper Curve, Stronger Egg", Inside Science, printed Jan. 21, 2016, http://www.insidescience.org/content/sharper-curve-stronger-egg/779, 6 pages.
Sigma reference 2007.
Sigma-Aldrich, Polyhydroxy compounds webpage, captured May 28, 2009.
Sunflower Oil, at https//en.wikipedia.org/wiki/Sunflower_oil (downloaded Sep. 19, 2017, pp. 1-8.
Supplementary European Search Report for Application No. 05 80 2894, dated Jul. 27, 2011.
Supplementary European Search Report for Application No. 05 800 844, dated Aug. 19, 2011.
Supplemetary European Search Report for EP Application No. 08782511, dated Apr. 3 2013.
Sweetman, Sean C., "Martindale: The complete drug reference," 33rd ed., 2002, Pharmaceutical Press, pp. 1-90.
The Lipid Handbook, 2nd edision, 1994, Tocopherols, pp. 129-131.
Wanasundara et al., "Effect of processing on constituents and oxidative stability of marine oils," Journal of Food Lipids, 1998, vol. 5, pp. 29-41.
Web article from http://www.buchi.com, "Slip Melting Point Determination of Palm Stearin", 1 page.
"What are hydrogenated fats?" at http://www.whfoods.comigenpage.php?tname=george&dbid=10 (downloaded Dec. 19, 2017), 3 pages.
9.1 Terminology for Vegetable Oils and Animal Fats, at http://www.e-education.psu.edu/egee439/node/683 (downloaded Sep. 13, 2017), pp. 1-8.
Advisory Action of U.S. Appl. No. 11/238,554, dated Jul. 10, 2009.
Ali, Handbook of Industrial Chemistry: Organic Chemicals, Chapter 4, Edible Fats, Oils and Waxes, 1994, pp. 85-121.
American heritage desk dictionary, 1981 p. 799, 2 pages.
Aqualon: Sodium Carboxymethylcellulose: Physical and Chemical Properties, Hercules Incorporated, 1999, 30 pages.
Bard FDA 510K Approval (Jan. 2001).
Bard FDA 510K Approval (Jul. 2002).
Bard Internet Publication (Apr. 2001).
Bellon et al., "Evaluation of a New Composite Prosthesis (PL-PU99) for the Repair of Abdominal Wall Defects in Terms of Behavior at the Peritoneal Interface," World Journal of Surgery, 26: 661-666 (2002).
Bendavid et al., "A Femoral 'Umbrella' for Femoral Hernial Repair Surgery," Gynecology and Obstetrics, 165: 153-156 (1987).
Bendavid et al., "New Techniques in Hernia Repair," World Journal of Surgery, 13: 522-531 (1989).
Zanter, Sheryl, "Chemistry of Cast Iron Seasoning: A Science-Based How-To," retrieved from sherylcanter.com on Apr. 5, 2013, pp. 1-5.
Clauss, Wolfram et al., "No Difference Among Modern Contract Media's Effect on Neointimal Proliferation and Restenosis After Coronary Stenting in Pigs," Investigative Reporting.
Copy of Extended European Search Report dated Dec. 10, 2015 issued for EP Patent Application No. 13804477, 3 pages.
CRC Handbook of Chemistry and Physics, 89th Edition, 2008-2009, Composition and Properties of Common Oils and Fats, pp. 7-9 to 7-13.
De Scheerder et al., "Experimental Study of Thrombogenicity and Foreign Body Reaction Induced by Heparinaoated Coronary Stents," Circulation, 1997, vol. 95, pp. 1549-1553.
De Scheerder et al., "Local Angiopeptin Delivery Using Coated Stents Reduces Neointimal Proliferation in Overstretched Porcine Coronary Arteries," J. Invasive Cardiol., 1995, vol. 8, pp. 215-222.
Drugs.com "Drug Index A to Z," retrieved on Apr. 1, 2013, pp. 1-4.
EP Office Action for EP Application No. 07838216.5, dated Feb. 11, 2010.
ESR for EP Application 05012112, dated Jul. 5, 2005.
ESR for EP Application 10157210, dated May 20, 2010.
European Communication for Application No. 07112611.4-2107, dated Nov. 30, 2007.
Fatty Acid Composition of Marine Oils by GLC, AOCS Official Method Ce 1b-89 (2009), pp. 1-7.
Fei, Bin, et al., "Hydrogel of Biodegradable Cellulose Derivatives. I. Radiation-Induced Crosslinking of CMC", Journal of Applied Polymer Science, 2000, vol. 78, pp. 278-283.

(56) References Cited

OTHER PUBLICATIONS

Final OA for U.S. Appl. No. 11/140,811 dated Nov. 25, 2009.
Final Office Action for U.S. Appl. No. 12/401,243 (listed on SB-08 as U.S. 2010/0233232), dated Jun. 11, 2012.
Final Office Action for U.S. Appl. No. 11/250,768, dated Nov. 9, 2010.
Final Office Action issued in U.S. Appl. No. 16/165,628 dated Apr. 13, 2020, 9 pages.
Garner, Brian a., "A Dictionary of Modern Legal Usage," 2nd ed., 1987, pp. 389-390 and 713-717.
Gervajio "Fatty Acids and Derivatives from Coconut Oil." Baileys Industrial Oil and Fat Products, Sixth Edition. Ed. Sahandi. Hoboken: John Wiley & Sons, Inc. 2005 1-3.
Goodnight et al., "Polyunsaturated Fatty Acids, Hyperlipidemia, and Thrombosis," 1982, American Heart Association, Journal of the American Heart Association, vol. 2, No. 2, pp. 87-113.
Greenawalt et al., "Evaluation of Sepramesh Biosurgical Composite in a Rabbit Hernia Repair Model," Journal of Surgical Research, 94: 92-98 (2000).
Hawley's Condensed Chemical Dictionary—pp. 425 and 426 (2001), which corresponds to "Exhibit Al.".
Helfrich et al., "Abdominal Wall Hernia Repair: Use of the Gianturco-Helfrich-Eberhach Hernia Mesh," Journal of Laparoendoscopic Surgery, 5(2): 91-96 (1995).
Henderson, R. James et al., "Hydrolysis of Fish Oils Containing Polymers of Triacylglycerols by Pancreatic Lipase in vitro", Lipids, vol. 28, No. 4, 1993, pp. 313-319.
Hercules Inc./Aqualon Div. CMC Quality Specifiction, Oct. 19, 2001 (Revised Sep. 2, 2008), 1 page.
Hoefler, Andrew C., "Sodium Carboxymethyl Cellulose: Chemistry, Functionality, and Applications", Hercules Incorporated, http://www.herc.com/foodgums/index.htm, 15 pages.
Hydrogenated Castor Oil, at http://www.acme-hardesty.com/product/hydrogenated-castor-oil/ (downloaded Jun. 2, 2017), which corresponds to "Exhibit B1".
International Preliminary Report on Patentability for Application No. PCT/US08/71565, dated Apr. 5, 2010.
International Preliminary Report on Patentability for Application No. PCT/US08/85386, dated Apr. 12, 2011.
International Search Report for Application No. PCT/US10/048167, dated Oct. 20, 2010.
Interview summary for U.S. Appl. No. 11/236,908 (listed on SB/08 as US 2006/0067974) dated Dec. 2, 2010.
Interview summary for U.S. Appl. No. 11/237,420 (listed on SB08a as US 2006/0078586) dated May 5, 2009.
ISR for PCT/BE02/00166, dated Apr. 3, 2003.
John McMurray, Organic Chemistry, third edition, 1992, pp. 45-48.
Kaczynski, Jason, "Natural Omega3 Fish Oil Supplements—How to Avoid Synthetic Fish Oils," accessed online at http://ezinearticles.com/?Natural-Omega3-Fish-Oil-Supplements—How-to-Avoid-Synthetic-Fish-Oils&id=2460278, Jun. 10, 2009.
Kugel, et al., "Minimally invasive, Nonlaparoscopic, Preperitoneal, and Sutureless, Inguinal Herniorraphy," The Journal of Surgery, 1999, vol. 178, pp. 298-302.
Lichtenstein, et al., "Repair of Recurrent Ventral Hernias by an Internal Binder," The American Journal of Surgery, 1976, vol. 132, pp. 121-125.
Luostarinen et al., "Vitamin E supplementation counteracts the fish oil induced increase of blood glucose in humans," Nutrition Research, vol. 15, No. 7, pp. 953-968, 1995.
Moreno et al., J. Agric. Food Chem., 2003, vol. 51, pp. 2216-2221.
Extended European Search Report issued in EP Application No. 18000936.7 dated Jan. 7, 2020, 9 pages.
Non-Final Office Action issued in U.S. Appl. No. 16/213,823 dated Feb. 14, 2020, 14 pages.
Van Den Berg et al., Chemical changes in curing and ageing oil paints, Icom Committee for Conservation, 1999, 248-253, vol. 1.
Office Action issued in EP Application No. 10825447.5 dated Feb. 20, 2020, 4 pages.
Non-Final Office Action issued in U.S. Appl. No. 15/817,018, dated Feb. 6, 2020, 28 pages.
Benchabane et al., Rheological properties of carboxymethyl cellulose (CMC) solutions, Colloid Polym Sci, 2008, 1173-1180, 286.
Non-Final Office Action issued in U.S. Appl. No. 16/165,628, dated Oct. 28, 2019.
Office Action issued in Chinese Application No. 201610997993.3 dated May 11, 2020, 7 pages.
Chinese Office Action (with English translation) dated Apr. 28, 2020 during the prosecution of corresponding Chinese Patent Application No. 201610998395.8, 14 pages.
Bruno, Gene, Omega-3 Fatty Acids, Literature Education Series on Dietary Supplements, Huntington College of dealth Sciences, 2009, 1-4.
Evans, D.F. et al., Measurement of gastrointestinal pH profiles in normal ambulant human subjects, Gut, 1988, 1035-1041, 29.
Hogg, Ronald J., et al., Clinical Trial to Evaluate Omega-3 Fatty Acids and Alternate Day Prednisone in Patients with IgA Nephropathy: Report from the Southwest Pediatric Nephrology Study Group, Clinical Journal of the American Society of Nephrology, 2006, 467-474, 1.
Mateo, R.D., et al., Effect of dietary supplementation of n-3 fatty acids and elevated concentrations of dietary protein on the performance of sows, J. Anim. Sci., 2009, 948-959, 87.
Etrovic, Z. S., Polymers from biological oils, Contemporary Materials, 1-1, 2010, 39-50.
Bann!, Vasav, et al., a Review on Spider Silk Adhesion, the Journal of Adhesion, 2011, 595-614, 87.

* cited by examiner

CURED GEL AND METHOD OF MAKING

RELATED APPLICATIONS

This application is a divisional of U.S. patent application Ser. No. 14/511,756 filed Oct. 10, 2014, which is a continuation of U.S. Non-Provisional application Ser. No. 11/237,263, filed Sep. 28, 2005, now U.S. Pat. No. 8,858,978, which claims priority to, and the benefit of, U.S. Provisional Application No. 60/613,808, filed Sep. 28, 2004, for all subject matter common to both applications. The disclosure of the provisional application and each of the above-mentioned non-provisional applications and patents are hereby incorporated by reference in its entirety. This application also relates to co-pending U.S. patent application Ser. No. 11/237,420, filed on Sep. 28, 2005, now U.S. Pat. No. 9,801,913 which application is hereby incorporated by reference in its entirety.

FIELD OF THE INVENTION

The present invention relates to coatings for medical devices, or films, which are cured, and more particularly to a method of curing a coating or stand alone film formed at least in part of a non-polymeric cross-linked gel cured a desired amount, and the resulting structure provided by the curing process.

BACKGROUND OF THE INVENTION

Coatings and drugs, agents, or compounds are utilized in combination with a number of medical devices, and in particular with implantable medical devices such as stents, stent-grafts, surgical meshes, vascular grafts, and the like. Other devices such as vena cava filters and anastomosis devices may also be used with coatings having drugs, agents, or compounds therein. In addition, surgical medical film is often used in surgical settings, such as in patients undergoing abdominal or pelvic laparotomy as an adjunct intended to reduce the incidence, extent, and severity of postoperative adhesions between different tissues and organs and implantable medical devices such as soft tissue support membranes and mesh.

In general, such coatings and films are manufactured utilizing polymeric based materials. The coatings and films are formed using a number of different manufacturing techniques. However, there has been little progress in the manufacture of coatings or films utilizing non-polymeric based materials in a manner that can form the desired coating or film, with desired degradation properties, while maintaining some of the anti-inflammatory, non-inflammatory, and wound healing properties of some of the non-polymeric substances available.

More specifically, oils are occasionally briefly mentioned as being a potential carrier component for the delivery of a therapeutic from a medical device. However, there has been little development with regard to the determination of how to accomplish the provision of a non-polymeric coating containing a therapeutic, or even a non-polymeric coating maintaining its original anti-inflammatory, non-inflammatory, or wound healing properties. Some of these anti-inflammatory, non-inflammatory, and wound healing characteristics can be found in oils containing fatty acids, especially omega-3 fatty acids, such as fish oil. However, there is little known relating to methods for configuring non-polymeric coatings to carry therapeutic agents in a manner that results in a predefined, desired, rate of degradation to provide for the controlled release of the therapeutic agent or the controlled degradation of the coating.

SUMMARY OF THE INVENTION

What is desired is a method of making a non-polymeric biological oil based coating on a medical device or in the form of a stand alone film, which exhibits properties such as anti-adhesion, anti-inflammation, non-inflammation, and enhanced wound healing, to the local tissue that can also be further enhanced with the application of one or more therapeutic agents or medications for absorption into the tissue that is in contact with the coating or film. The method of making directly influences the resulting coating or film and corresponding rate of degradation of the coating or film following implantation, and thus the controlled release of any therapeutic agents contained within. The method of curing also influences the level of inherent anti-inflammation, non-inflammation, and wound healing properties of certain biological oils that is able to be maintained after curing. The present invention is directed toward further solutions to address this need.

Curing with respect to the present invention generally refers to thickening, hardening, or drying of a material brought about by heat, UV, or chemical means.

In accordance with one embodiment of the present invention, a method of curing to form a gel includes providing a non-polymeric substance to be cured. An amount of cross-linking desired within the substance as a result of curing is determined. Heat is applied at a selected temperature for a selected time period based on the determination of amount of cross-linking desired to achieve the desired amount of cross-linking within the substance to form the gel.

In accordance with aspects of the present invention, the substance to be cured can be an oil or oil composition. The substance to be cured can contain fatty acids. The substance to be cured can include at least one therapeutic agent. The agent can be any one or more of antioxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, prodrugs, and antiseptics.

In accordance with further aspects of the present invention, the step of determining includes selecting the amount of cross-linking based on a desired rate of degradation of the gel following implantation. The application of heat occurs at a relatively higher temperature if more cross-linking is desired and at a relatively lower temperature if a lesser amount of cross-linking is desired. The application of heat occurs for a relatively greater duration of time if more cross-linking is desired and at a relatively lesser duration of time if a lesser amount of cross-linking is desired. A relatively faster rate of degradation provides for a relatively faster release of therapeutic agent contained within the gel, while a relatively slower rate of degradation provides for a relatively slower and more controlled release of therapeutic agent contained within the gel.

In accordance with aspects of the present invention, a relatively lesser amount of cross-links provides a relatively faster rate of degradation which provides for a relatively faster release of therapeutic agent contained within the gel, while a relatively greater amount of cross-links provides a relatively slower rate of degradation which provides for a relatively slower and more controlled release of therapeutic agent contained within the gel.

In accordance with one embodiment of the present invention, curing at a relatively greater temperature for a relatively lesser amount of time results in a greater amount of cross-linking within the substance than curing at a relatively lesser temperature for a relatively greater amount of time.

In accordance with further aspects of the present invention, the non-polymeric substance to be cured at least partially includes at least partially cured oil to reduce the amount of time required to achieve the desired amount of cross-linking. The substance can further include other oils, such as linseed oil or tung oil, as well as free fatty acids to reduce the amount of time required to achieve the desired amount of cross-linking.

In accordance with further aspects of the present invention, the cross-linked gel is configured to provide controlled release of a therapeutic agent component. The cross-linked gel is bio-absorbable. The cross-linked gel maintains at least one property, such as anti-inflammatory properties, non-inflammatory properties, and wound healing properties.

It should be noted that the term cross-linked gel, as utilized herein with reference to the present invention, refers to a gel that is non-polymeric and is derived from an oil composition comprising molecules covalently cross-linked into a three-dimensional network by one or more of ester, ether, peroxide, and carbon-carbon bonds in a substantially random configuration. In various preferred embodiments, the oil composition comprises a fatty acid molecule, a glyceride, and combinations thereof.

In accordance with further aspects of the present invention, the method can include sterilizing the cross-linked gel with a method of sterilization, such as ethylene oxide, gamma radiation, e-beam, steam, gas plasma, or vaporized hydrogen peroxide (VHP).

In accordance with one embodiment of the present invention, a heat cured non-polymeric gel includes a collection of non-polymeric cross-links resulting from application of heat for a selected temperature for a selected duration to achieve a desired amount of cross-linking to form the non-polymeric gel.

In accordance with aspects of the present invention, the gel can be derived from an oil or oil composition. The gel can be derived from a substance comprising fatty acids. The gel can include at least one therapeutic agent. The agent can be any one or more of antioxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, prodrugs, and antiseptics.

In accordance with further aspects of the present invention, the gel is configured to maintain a desired rate of degradation of the gel following implantation. The gel is formed with application of heat at a relatively higher temperature if more cross-linking is desired and at a relatively lower temperature if a lesser amount of cross-linking is desired. The gel is formed with application of heat for a relatively greater duration of time if more cross-linking is desired and at a relatively lesser duration of time if a lesser amount of cross-linking is desired.

In accordance with further aspects of the present invention, the gel is formed from at least partially pre-cured oil to reduce the amount of time required to achieve the desired amount of cross-linking. The cross-linked gel is configured to provide controlled release of a therapeutic agent component. The cross-linked gel is bio-absorbable. The cross-linked gel maintains at least one property, such as anti-inflammatory properties, non-inflammatory properties, or wound healing properties.

In accordance with further aspects of the present invention, the gel has been sterilized with a method of sterilization including ethylene oxide, gamma radiation, e-beam, steam, gas plasma, or vaporized hydrogen peroxide (VHP).

In accordance with further aspects of the present invention, the gel is configured as a coating on a medical device or as a stand-alone film.

BRIEF DESCRIPTION OF THE DRAWINGS

The aforementioned features and advantages, and other features and aspects of the present invention, will become better understood with regard to the following description and accompanying drawings, wherein.

DETAILED DESCRIPTION

Figure 1:
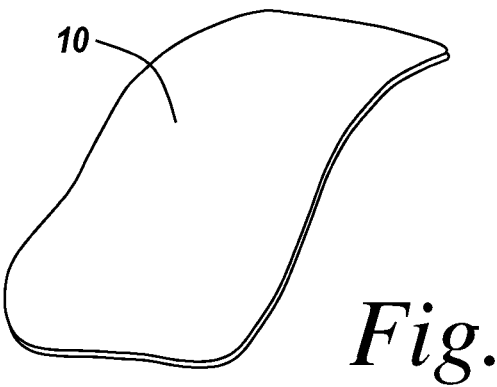
FIG. 1 is a diagrammatic illustration of a cross-linked gel realized as a stand alone film, according to one embodiment of the present invention.

An illustrative embodiment of the present invention relates to the provision of a coating or film that is a cured cross-linked gel and can exhibit anti-inflammatory properties, non-inflammatory properties, anti-adhesion properties, and/or wound healing properties, and corresponding method of making. The cross-linked gel can be its own medical device (i.e., a stand alone film), or the cross-linked gel can be combined with another medical device to provide the desired characteristics, in addition to potentially delivering therapeutic agents. The cross-linked gel is generally formed of a naturally occurring oil, or an oil composition formed in part of a naturally occurring oil having fatty acids. In addition, the oil composition can include a therapeutic agent component, such as a drug or other bioactive agent. The cross-linked gel is implantable in a patient, or applied on the skin surface of the patient, for short term or long term applications, and can include controlled release of the therapeutic agent. As implemented herein, the cross-linked gel is a non-polymeric cross-linked gel derived at least in part from a fatty acid compound.

As utilized herein, the term "bio-absorbable" generally refers to having the property or characteristic of being able to penetrate the tissue of a patient's body. In certain embodiments of the present invention bio-absorption occurs through a lipophilic mechanism. The bio-absorbable substance is soluble in the phospholipid bi-layer of cells of body tissue, and therefore impacts how the bio-absorbable substance penetrates into the cells.

It should be noted that a bio-absorbable substance is different from a biodegradable substance. Biodegradable is generally defined as capable of being decomposed by biological agents, or capable of being broken down by microorganisms or biological processes, in a manner that does not result in cellular uptake of the biodegradable substance. Biodegradation thus relates to the breaking down and distributing of a substance through the patient's body, verses the penetration of the cells of the patient's body tissue. Biodegradable substances, such as polymers, can cause inflammatory response due to either the parent substance or those substances formed during breakdown, and they may or may not be absorbed by tissues. Bio-absorbable substances break down into substances or components that do not cause an inflammatory response and can be consumed by the cells forming the body tissues.

The phrase "controlled release" generally refers to the release of a biologically active agent in a predictable manner over the time period of weeks or months, as desired and predetermined upon formation of the biologically active agent on the medical device from which it is being released. Controlled release includes the provision of an initial burst of release upon implantation, followed by the predictable release over the aforementioned time period.

With regard to the aforementioned oils, it is generally known that the greater the degree of unsaturation in the fatty acids the lower the melting point of a fat, and the longer the hydrocarbon chain the higher the melting point of the fat. A polyunsaturated fat, thus, has a lower melting point, and a saturated fat has a higher melting point. Those fats having a lower melting point are more often oils at room temperature. Those fats having a higher melting point are more often waxes or solids at room temperature. Therefore, a fat having the physical state of a liquid at room temperature is an oil. In general, polyunsaturated fats are liquid oils at room temperature, and saturated fats are waxes or solids at room temperature.

Polyunsaturated fats are one of four basic types of fat derived by the body from food. The other fats include saturated fat, as well as monounsaturated fat and cholesterol. Polyunsaturated fats can be further composed of omega-3 fatty acids and omega-6 fatty acids. Under the convention of naming the unsaturated fatty acid according to the position of its first double bond of carbons, those fatty acids having their first double bond at the third carbon atom from the methyl end of the molecule are referred to as omega-3 fatty acids. Likewise, a first double bond at the sixth carbon atom is called an omega-6 fatty acid. There can be both monounsaturated and polyunsaturated omega fatty acids.

Omega-3 and omega-6 fatty acids are also known as essential fatty acids because they are important for maintaining good health, despite the fact that the human body cannot make them on its own. As such, omega-3 and omega-6 fatty acids must be obtained from external sources, such as food. Omega-3 fatty acids can be further characterized as containing eicosapentaenoic acid (EPA), docosahexanoic acid (DHA), and alpha-linolenic acid (ALA). Both EPA and DHA are known to have anti-inflammatory effects and wound healing effects within the human body.

Oil that is hydrogenated becomes a waxy solid. Attempts have been made to convert the polyunsaturated oils into a wax or solid to allow the oil to adhere to a device for a longer period of time. One such approach is known as hydrogenation, which is a chemical reaction that adds hydrogen atoms to an unsaturated fat (oil) thus saturating it and making it solid at room temperature. This reaction requires a catalyst, such as a heavy metal, and high pressure. The resultant material forms a non-cross-linked semi-solid. Hydrogenation can reduce or eliminate omega-3 fatty acids, and any therapeutic effects (both anti-inflammatory and wound healing) they offer.

For long term controlled release applications, polymers, as previously mentioned, have been utilized in combination with a therapeutic agent. Such a combination provides a platform for the controlled long term release of the therapeutic agent from a medical device. However, polymers have been determined to themselves cause inflammation in body tissue. Therefore, the polymers often must include at least one therapeutic agent that has an anti-inflammatory effect to counter the inflammation caused by the polymer delivery agent. In addition, patients that received a polymer-based implant must also follow a course of long term systemic anti-platelet therapy, on a permanent basis, to offset the thrombogenic properties of the non-absorbable polymer. A significant percentage of patients that receive such implants are required to undergo additional medical procedures, such as surgeries (whether related follow-up surgery or non-related surgery) and are required to stop their anti-platelet therapy. This can lead to a thrombotic event, such as stroke, which can lead to death. Use of the inventive coating described herein can negate the necessity of anti-platelet therapy, and the corresponding related risks described, because there is no thrombogenic polymer reaction to the coating. Other polymer implant patients must follow a course of systemic anti-inflammatory therapy, to offset the inflammatory properties of the non-absorbable polymer. Typical anti-inflammatory agents are immunosupressants and systemic delivery of anti-inflammatory agents can sometimes lead to additional medical complications, such as infection or sepsis, which can lead to long term hospitalization or death. Use of the non-polymeric cross-linked gel of the inventive coating described herein may also negate the necessity of anti-inflammatory therapy, and the corresponding related risks described, because there is no inflammatory reaction to an oil-based coating or film formed in accordance with the present invention.

In addition, some curing methods have been indicated to have detrimental effects on the therapeutic agent combined with the omega-3 fatty acid, making them partially or completely ineffective. As such, oils, and more specifically oils containing omega-3 fatty acids, have been utilized as a delivery agent for the short term uncontrolled release of a therapeutic agent, so that minimal or no curing is required. However, there are no known uses of oils containing omega-3 fatty acids for combination with a therapeutic agent in a controlled release application that makes use of the therapeutic benefits of the omega-3 fatty acids. Further, some heating of the omega-3 fatty acids to cure the oil can lessen the total therapeutic effectiveness of the omega-3 fatty acids, but not eliminate the therapeutic effectiveness. One characteristic that can remain after certain curing by heating methods is the non-inflammatory response of the tissue when exposed to the cured omega-3 fatty acid material. As such, an oil containing omega-3 fatty acids can be heated for curing purposes, and still maintain some or even a majority of the therapeutic effectiveness of the omega-3 fatty acids. In addition, although the therapeutic agent combined with the omega-3 fatty acid and cured with the omega-3 fatty acid can be rendered partially ineffective, the portion remaining of the therapeutic agent can, in accordance with the present invention, maintain pharmacological activity and in some cases be more effective than an equivalent quantity of agent delivered with other barrier or coating materials.

It should be noted that as utilized herein to describe the present invention, the terms vitamin E, vitamin E compound, and alpha-tocopherol, are intended to refer to the same or substantially similar substance, such that they are interchangeable and the use of one includes an implicit reference to both. Further included in association with the term vitamin E are such variations including but not limited to one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed tocopherols, vitamin E TPGS, derivatives, analogs and pharmaceutically acceptable salts thereof.

FIGS. 1 through 11, wherein like parts are designated by like reference numerals throughout, illustrate an example embodiment of a non-polymeric biological oil cross-linked gel cured to form a coating or film using heat according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

FIG. 1 illustrates a non-polymeric cross-linked gel 10 in accordance with one embodiment of the present invention. The cross-linked gel 10 is flexible, to the extent that it can be placed in a flat, curved, or rolled, configuration within a patient. The cross-linked gel 10 is implantable, for both short term and long term applications. Depending on the particular formulation of the cross-linked gel 10, the cross-linked gel 10 will be present after implantation for a period of hours to days, or possibly months.

The cross-linked gel 10 is formed of an oil component. The oil component can be either an oil, or an oil composition. The oil component can be a naturally occurring oil, such as fish oil, cod liver oil, cranberry oil, or other oils having desired characteristics. One example embodiment of the present invention makes use of a fish oil in part because of the high content of omega-3 fatty acids, which provide healing support for damaged tissue, as discussed below. The fish oil also serves as an anti-adhesion agent. In addition, the fish oil maintains anti-inflammatory or non-inflammatory properties as well. The present invention is not limited to formation of the gel with fish oil as the naturally occurring oil. However, the following description makes reference to the use of fish oil as one example embodiment. Other naturally occurring oils can be utilized in accordance with the present invention as described herein.

It should be noted that as utilized herein, the term fish oil fatty acid includes but is not limited to omega-3 fatty acid, fish oil fatty acid, free fatty acid, esters of fish oil, triglycerides, or a combination thereof. The fish oil fatty acid includes one or more of arachidic acid, gadoleic acid, arachidonic acid, eicosapentaenoic acid, docosahexaenoic acid or derivatives, analogs and pharmaceutically acceptable salts thereof. Furthermore, as utilized herein, the term free fatty acid includes but is not limited to one or more of butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, analogs and pharmaceutically acceptable salts thereof. The naturally occurring oils, including fish oil, are cured as described herein to form a hydrophobic cross-linked gel, creating the cross-linked gel 10.

It should further be noted that FIG. 1 represents merely one embodiment of the cross-linked gel 10. The cross-linked gel 10 serves as a biological oil barrier and, depending on degree of cure, can also serve as a physical barrier, as depicted. The biological oil barrier is represented by the application of the fatty acid based oil, such as fish oil, onto a medical device. Such a configuration provides a biological oil cross-linked gel that provides a non-inflammatory or anti-inflammatory barrier coating. Using a number of different methods as described below, the biological oil can be cured to create a non-polymeric cross-linked gel. In the instance of the medical device taking the form of a surgical mesh, the biological oil can be cured to the extent that the cells or pores of the mesh are substantially or completely bridged by the cured biological oil creating a physical barrier. With such a configuration there remains some biological oil that is not cured but is interdispersed within the cured oil and maintains the biological oil cross-linked gel as well. Thus, substantial curing creates both a biological oil cross-linked gel and a physical barrier. The physical barrier provides anti-adhesive properties of the barrier as discussed herein. Additional embodiments can include the provision of the substantially cured oil forming the biological oil cross-linked gel with physical layer, and then a subsequent application of the biological oil as a top coat. This creates a more substantial biological oil cross-linked gel supported by the combination biological oil cross-linked gel and physical cross-linked gel.

One aspect of the cross-linked gel 10 mentioned above is that it has anti-adhesion characteristics or properties. By anti-adhesion, what is meant is a characteristic whereby the incidence, extent, and severity of postoperative adhesions, or lacerations or other tissue injuries, between different tissues and organs is reduced. The anti-adhesion characteristic results from the materials used to form the cross-linked gel 10.

More specifically, the cross-linked gel 10 provides a lubricious or anti-adhesive surface against tissue. The cross-linked gel 10 itself, in its substantially cured configuration, can provide a physical anti-adhesion barrier between two sections of tissue, or the cross-linked gel 10 can form an anti-adhesion surface on a medical device, such as the mesh 40. The use of the naturally occurring oil, such as fish oil, provides extra lubrication to the surface of the medical device, which helps to reduce injury. With less injury, there is less of an inflammatory response, and less healing required. The biological oil barrier created by the fatty acid oil derived cross-linked gel likewise provides anti-inflammatory properties and non-inflammatory properties, thus reducing the occurrence of inflammatory response and also adhesions due to inflammation. The oily surface of the cross-linked gel 10 provides the anti-adhesion characteristics. One of ordinary skill in the art will appreciate that different oils will have different anti-adhesive properties, and the oils can be modified to be more liquefied or more solid or waxy, as desired. Accordingly, the degree of anti-adhesive properties offered by the cross-linked gel 10 can vary. The modification of the oils from a more liquid physical state to a more solid, but still flexible, physical state is implemented through the curing process. As the oils are cured, especially in the case of fatty acid-based oils such as fish oil, cross-links form creating a gel. As the curing process is performed over increasing time durations and/or increasing temperature conditions, more cross-links form transitioning the gel from a relatively liquid gel to a relatively solid-like, but still flexible, gel structure.

Another aspect of the present invention is that the cross-linked gel 10 is formed of the bio-absorbable material, such as naturally occurring fish oil, in accordance with the example embodiment described herein. The bio-absorbable properties of the naturally occurring oil enable the cross-linked gel 10 to be absorbed by the cells of the body tissue (i.e., bio-absorbable). In example embodiments of the present invention, the bio-absorbable cross-linked gel contains lipids, many of which originate as triglycerides. It has previously been demonstrated that triglyceride byproducts, such as partially hydrolyzed triglycerides and fatty acid molecules can integrate into cellular membranes and enhance the solubility of drugs into the cell. Whole triglycerides are known not to enhance cellular uptake as well as partially hydrolyzed triglyceride, because it is difficult for whole triglycerides to cross cell membranes due to their relatively larger molecular size. Vitamin E compounds can also integrate into cellular membranes resulting in decreased membrane fluidity and cellular uptake.

Compounds that move too rapidly through a tissue may not be effective in providing a sufficiently concentrated dose in a region of interest. Conversely, compounds that do not migrate in a tissue may never reach the region of interest. Cellular uptake enhancers such as fatty acids and cellular uptake inhibitors such as alpha-tocopherol can be used alone or in combination to provide an effective transport of a given compound to a given region or location. Both fatty acids and alpha-tocopherol are accommodated by the cross-linked gel of the present invention described herein. Accordingly, fatty acids and alpha-tocopherol can be combined in differing amounts and ratios to contribute to a cross-linked gel in a manner that provides control over the cellular uptake characteristics of the cross-linked gel and any therapeutic agents mixed therein.

For example, the amount of alpha-tocopherol can be varied in the cross-linked gel. Alpha-tocopherol (vitamin E compound) is known to slow autoxidation in fish oil by reducing hydroperoxide formation, which results in a decrease in the amount of cross-linking in cured fish oil. It has been shown that even with fewer cross-links, the addition of varying amounts of alpha-tocopherol can be used to increase the time in which the cross-linked gel degrades compared to a cross-linked gel of fish oil alone. The addition of alpha-tocopherol to the oil or oil composition prior to forming the cross-linked gel can result in fewer cross-links when compared with the oil without alpha-tocopherol. Although there are fewer cross-links, the degradation period is extended with the alpha-tocopherol added. In addition alpha-tocopherol can be used to increase solubility of drugs in the fish oil forming the cross-linked gel. Thus, varying the amount of alpha-tocopherol present in the cross-linked gel can impact the resulting formation. Alpha-tocopherol can actually protect the therapeutic drug during curing, which increases the resulting drug load in the cross-linked gel after curing. Furthermore, with certain therapeutic drugs, the increase of alpha-tocopherol in the cross-linked gel serves to slow and extend drug release due to the increased solubility of the drug in the alpha-tocopherol component of the cross-linked gel. This reflects the cellular uptake inhibitor functionality of alpha-tocopherol, in that the uptake of the drug is slowed and extended over time.

It should further be emphasized that the bio-absorbable nature of the cross-linked gel results in the cross-linked gel 10 being completely absorbed over time by the cells of the body tissue. There are no substances in the cross-linked gel, or break down products of the cross-linked gel, that induce an inflammatory response. The cross-linked gel 10 is generally composed of, or derived from, omega-3 fatty acids bound to triglycerides, potentially also including a mixture of free fatty acids and vitamin E compounds (alpha-tocopherol). The triglycerides are broken down by lipases (enzymes) which result in free fatty acids that can than be transported across cell membranes. Subsequently, fatty acid metabolism by the cell occurs to metabolize any substances originating with the cross-linked gel. The bio-absorbable nature of the cross-linked gel of the present invention results in the cross-linked gel being absorbed over time, leaving only an underlying delivery or other medical device structure that is biocompatible. There is no foreign body inflammatory response to the bio-absorbable cross-linked gel.

Although the present invention is bio-absorbable to the extent that the cross-linked gel 10 experiences the uptake into or through body tissues, in the specific embodiment described herein formed using naturally occurring oils, the exemplar oils are also lipid based oils. The lipid content of the oils provides a highly bio-absorbable cross-linked gel 10. More specifically, there is a phospholipids layer in each cell of the body tissue. The fish oil, and equivalent oils, contain lipids as well. There is a lipophilic action that results where the lipids are attracted by each other in an effort to escape the aqueous environment surrounding the lipids.

A further aspect of the cross-linked gel 10 is that the specific type of oil can be varied, and can contain elements beneficial to healing. The cross-linked gel also provides a natural scaffold for cellular growth and remodeling with clinical applications in general surgery, spinal repair, orthopedic surgeries, tendon and ligament repairs, gynecological and pelvic surgeries, and nerve repair applications. The addition of therapeutic agents to the cross-linked gels used in these applications can be utilized for additional beneficial effects, such as pain relief or infection minimization. In addition, non-surgical applications include external wound care, such as a treatment for burns or skin ulcers, without therapeutics as a clean, non-permeable, non-adhesive, antiinflammatory, non-inflammatory dressing, or with added therapeutics for additional beneficial effects. The cross-linked gel may also be used as a transdermal drug delivery patch.

The process of wound healing involves tissue repair in response to injury and it encompasses many different biologic processes, including epithelial growth and differentiation, fibrous tissue production and function, angiogenesis, and inflammation. The inventive cross-linked gel has been shown in an animal model not to produce an inflammatory response, but still provide excellent cellular overgrowth with little to no fibrous capsule formation. Accordingly, the cross-linked gel provides an excellent material suitable for wound healing applications.

Another aspect of the cross-linked gel 10 mentioned above is that the cross-linked gel 10 can contain therapeutic agents for delivery to the body tissue. Therapeutic agents have been delivered to a targeted location in a human utilizing a number of different methods in the past. For example, agents may be delivered nasally, transdermally, intravenously, orally, or via other conventional methods. Delivery may vary by release rate (i.e., quick release or slow release). Delivery may also vary as to how the drug is administered. Specifically, a drug may be administered locally to a targeted area, or administered systemically.

As utilized herein, the phrase "therapeutic agent(s)" refers to a number of different drugs or agents available, as well as future agents that may be beneficial for use with the cross-linked gel of the present invention. Therapeutic agents can be added to the cross-linked gel 10, and/or the medical device in combination with the cross-linked gel 10 as discussed herein. The therapeutic agent component can take a number of different forms including anti-oxidants, anti-inflammatory agents, anti-coagulant agents, drugs to alter lipid metabolism, anti-proliferatives, anti-neoplastics, tissue growth stimulants, functional protein/factor delivery agents, anti-infective agents, anti-imaging agents, anesthetic agents, therapeutic agents, tissue absorption enhancers, anti-adhesion agents, germicides, anti-septics, analgesics, prodrugs, and any additional desired therapeutic agents such as those listed in Table 1 below.

TABLE #1

| CLASS | EXAMPLES |
|---|---|
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids (e.g. dexamethazone, methylprednisolone), leflunomide, NSAIDS, ibuprofen, acetaminophen, hydrocortizone acetate, hydrocortizone sodium phosphate, macrophage-targeted bisphosphonates |
| Growth Factor Antagonists | Angiopeptin, trapidil, suramin |
| Antiplatelet Agents | Aspirin, dipyridamole, ticlopidine, clopidogrel, GP IIb/IIIa inhibitors, abcximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus micophenonolic acid, rapamycin, everolimus, tacrolimus, paclitaxel, QP-2, actinomycin, estradiols, dexamethasone, methatrexate, cilostazol, prednisone, cyclosporine, doxorubicin, ranpirnas, troglitzon, valsarten, pemirolast, C-MYC antisense, angiopeptin, vincristine, PCNA ribozyme, 2-chloro-deoxyadenosine |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyanoacrylate, hydrogels, collagen, liposomes |
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibitation of Protein Synthesis/ECM formation | Halofuginone, prolyl hydroxylase inhibitors, C-proteinase inhibitors |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, rifampin, mupirocin, RIP, kanamycin, brominated furonone, algae byproducts, bacitracin, oxacillin, nafcillin, floxacillin, clindamycin, cephradin, neomycin, methicillin, oxytetracycline hydrochloride, Selenium. |
| Gene Delivery | Genes for nitric oxide synthase, human growth hormone, antisense oligonucleotides |
| Local Tissue perfusion | Alcohol, H2O, saline, fish oils, vegetable oils, liposomes |
| Nitric oxide Donor Derivatives | NCX 4016 - nitric oxide donor derivative of aspirin, SNAP |

TABLE #1-continued

| CLASS | EXAMPLES |
|---|---|
| Gases | Nitric oxide, compound solutions |
| Imaging Agents | Halogenated xanthenes, diatrizoate meglumine, diatrizoate sodium |
| Anesthetic Agents | Lidocaine, benzocaine |
| Descaling Agents | Nitric acid, acetic acid, hypochlorite |
| Anti-Fibrotic Agents | Interferon gamma -1b, Interluekin - 10 |
| Immunosuppressive/ Immunomodulatory Agents | Cyclosporine, rapamycin, mycophenolate motefil, leflunomide, tacrolimus, tranilast, interferon gamma-1b, mizoribine |
| Chemotherapeutic Agents | Doxorubicin, paclitaxel, tacrolimus, sirolimus, fludarabine, ranpirnase |
| Tissue Absorption Enhancers | Fish oil, squid oil, omega 3 fatty acids, vegetable oils, lipophilic and hydrophilic solutions suitable for enhancing medication tissue absorption, distribution and permeation |
| Anti-Adhesion Agents | Hyaluronic acid, human plasma derived surgical sealants, and agents comprised of hyaluronate and carboxymethylcellulose that are combined with dimethylaminopropyl, ehtylcarbodimide, hydrochloride, PLA, PLGA |
| Ribonucleases | Ranpirnase |
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Antiseptics | Selenium |
| Analgesics | Bupivicaine, naproxen, ibuprofen, acetylsalicylic acid |

Some specific examples of therapeutic agents useful in the anti-restenosis realm include cerivastatin, cilostazol, fluvastatin, lovastatin, paclitaxel, pravastatin, rapamycin, a rapamycin carbohydrate derivative (for example, as described in US Patent Application Publication 2004/0235762), a rapamycin derivative (for example, as described in U.S. Pat. No. 6,200,985), everolimus, seco-rapamycin, seco-everolimus, and simvastatin. With systemic administration, the therapeutic agent is administered orally or intravenously to be systemically processed by the patient. However, there are drawbacks to a systemic delivery of a therapeutic agent, one of which is that the therapeutic agent travels to all portions of the patient's body and can have undesired effects at areas not targeted for treatment by the therapeutic agent. Furthermore, large doses of the therapeutic agent only amplify the undesired effects at non-target areas. As a result, the amount of therapeutic agent that results in application to a specific targeted location in a patient may have to be reduced when administered systemically to reduce complications from toxicity resulting from a higher dosage of the therapeutic agent.

Accordingly, an alternative to the systemic administration of a therapeutic agent is the use of a targeted local therapeutic agent delivery approach. With local delivery of a therapeutic agent, the therapeutic agent is administered using a medical device or apparatus, directly by hand, or sprayed on the tissue, at a selected targeted tissue location of the patient that requires treatment. The therapeutic agent emits, or is otherwise delivered, from the medical device apparatus, and/or carrier, and is applied to the targeted tissue location. The local delivery of a therapeutic agent enables a more concentrated and higher quantity of therapeutic agent to be delivered directly at the targeted tissue location, without having broader systemic side effects. With local delivery, the therapeutic agent that escapes the targeted tissue location dilutes as it travels to the remainder of the patient's body, substantially reducing or eliminating systemic side effects.

Targeted local therapeutic agent delivery using a medical device can be further broken into two categories, namely, short term and long term ranging generally within a matter of seconds or minutes to a few days or weeks to a number of months. Typically, to achieve the long term delivery of a therapeutic agent, the therapeutic agent must be combined with a delivery agent, or otherwise formed with a physical impediment as a part of the medical device, to slow the release of the therapeutic agent.

Prior attempts to create films and drug delivery platforms, such as in the field of stents, primarily make use of high molecular weight synthetic polymer based materials to provide the ability to better control the release of the therapeutic agent. Essentially, the polymer in the platform releases the drug or agent at a predetermined rate once implanted at a location within the patient. Regardless of how much of the therapeutic agent would be most beneficial to the damaged tissue, the polymer releases the therapeutic agent based on properties of the polymer. Accordingly, the effect of the therapeutic agent is substantially local at the surface of the tissue making contact with the medical device having the coating. In some instances the effect of the therapeutic agent is further localized to the specific locations of, for example, stent struts or mesh struts pressed against the tissue location being treated. These prior approaches can create the potential for a localized toxic effect.

The cross-linked gel 10 of the present invention, however, makes use of the natural oils to form a non-polymeric natural oil based therapeutic agent delivery platform, if desired. Furthermore, the cross-linked gel 10 can be formed in a manner that creates the potential for controlled long term release of a therapeutic agent, while still maintaining the benefits of the natural oil component of the cross-linked gel 10.

More specifically, it is known that oil that is oxygenated becomes a waxy solid. Attempts have been made to convert the polyunsaturated oils into a wax or solid to allow the oil to adhere to a device for a longer period of time. One such approach applies the oil to the medical device and allows the oil to dry.

With the present invention, and in the field of soft tissue applications, and in part because of the lipophilic mechanism enabled by the bio-absorbable lipid based cross-linked gel 10 of the present invention, the uptake of the therapeutic agent is facilitated by the delivery of the therapeutic agent to the cell membrane by the bio-absorbable cross-linked gel 10. Further, the therapeutic agent is not freely released into the body fluids, but rather, is delivered directly to the cells and tissue. In prior configurations using polymer based coatings, the drugs were released at a rate regardless of the reaction or need for the drug on the part of the cells receiving the drug.

In addition, when the oil provided to form the cross-linked gel 10 is a naturally occurring oil containing the omega-3 fatty acids (including DHA and EPA), the process for forming the cross-linked gel 10 can be tailored to avoid causing detrimental effects to the beneficial properties of the omega-3 fatty acids, or at least effects too detrimental to have any lasting effect. As described herein, certain properties of the fatty acids may lose their effectiveness, however other desired properties are maintained. If there is no concern for maintaining the beneficial effects, the curing and other steps leading to the formation of the cross-linked gel 10 can include steps that may reduce some of the beneficial properties of the omega-3 fatty acids, as understood by one of ordinary skill in the art. Example embodiments illustrating the formation and different configurations of the cross-linked gel 10 are provided herein.

The cross-linked gel 10 of the present invention serves as a non-polymeric biological oil based cross-linked gel and can also serve as a physical cross-linked gel if sufficiently cured. In accordance with the example embodiments described herein, the cross-linked gel is formed of a non-polymeric cross-linked gel derived from fatty acid compounds. The fatty acid compounds include omega-3 fatty acids when the oil utilized to form the cross-linked gel is fish oil or an analog or derivative thereof. As liquid fish oil is heated, autoxidation occurs with the absorption of oxygen into the fish oil to create hydroperoxides in an amount dependent upon the amount of unsaturated (C=C) sites in the fish oil. However, the (C=C) bonds are not consumed in the initial reaction. Concurrent with the formation of hydroperoxides is the isomerization of (C=C) double bonds from cis to trans in addition to double bond conjugation. It has been demonstrated that hydroperoxide formation increases with temperature. Heating of the fish oil allows for cross-linking between the fish oil unsaturated chains using a combination of peroxide (C—O—O—C), ether (C—O—C), and hydrocarbon (C=C) bridges. The formation of the cross-links results in gelation of the cross-linked gel after the (C=C) bonds have substantially isomerized into the trans configuration. The (C=C) bonds can also form C—C cross-linking bridges in the glyceride hydrocarbon chains using a Diels-Alder Reaction. In addition to solidifying the cross-linked gel through cross-linking, both the hydroperoxide and (C=C) bonds can undergo secondary reactions converting them into lower molecular weight secondary oxidation byproducts including aldehydes, ketones, alcohols, fatty acids, esters, lactones, ethers, and hydrocarbons.

Accordingly, the non-polymeric cross-linked gel derived from fatty acid compounds, such as those of fish oil, includes a cross-linked structure of triglyceride and fatty acid molecules in addition to free and bound glycerol, monoglyceride, diglyceride, and triglyceride, fatty acid, anhydride, lactone, aliphatic peroxide, aldehyde, and ketone molecules. There are a substantial amount of ester bonds remaining after curing in addition to peroxide linkages forming the majority of the cross-links in the gel. The cross-linked gel degrades into fatty acid, short and long chain alcohol, and glyceride molecules, which are all non-inflammatory and likewise consumable by cells in the soft tissue to which the cross-linked gel is applied. Thus, the cross-linked gel is bio-absorbable.

Figure 2A:
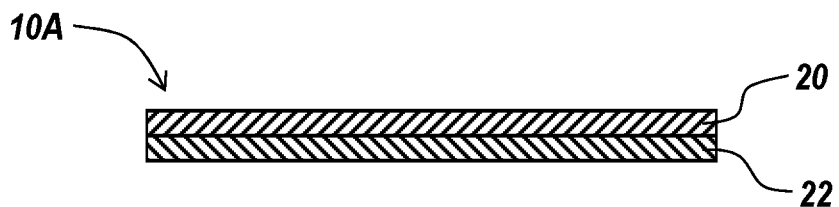
FIGS. 2A, 2B, and 2C are cross-sectional views of the cross-linked gel in accordance with one aspect of the present invention.
Figure 2B:
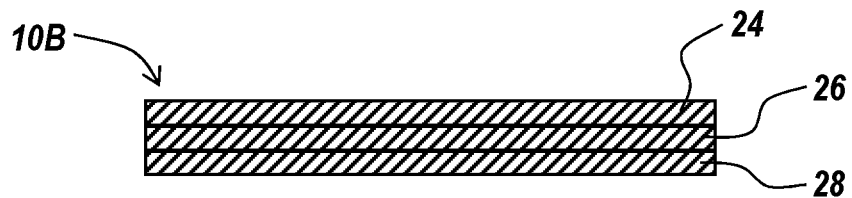
Figure 2C:
Figure 3A:
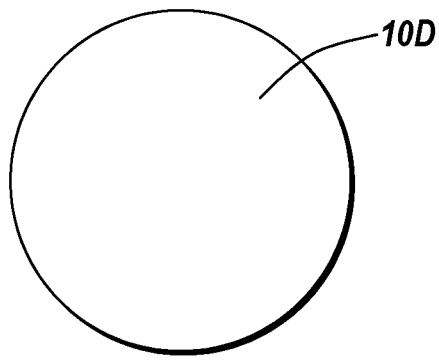
FIGS. 3A, 3B, 3C, 3D, 3E, and 3F are diagrammatic views of the cross-linked gel in accordance with another aspect of the present invention.
Figure 3B:
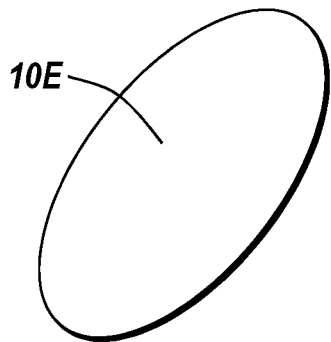
Figure 3C:
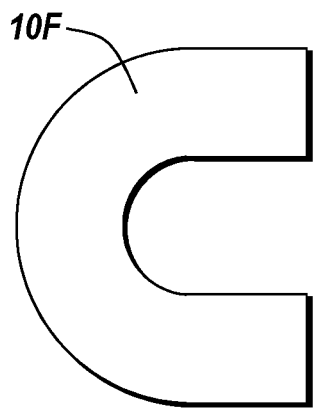
Figure 3D:
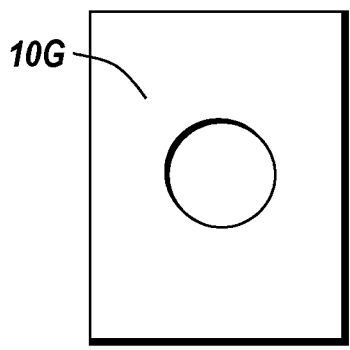
Figure 3E:
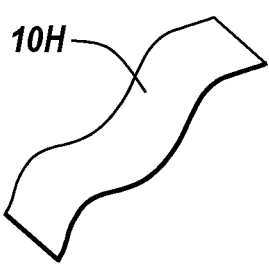
Figure 3F:
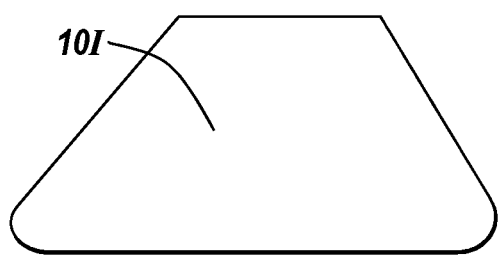

FIGS. 2A, 2B, and 2C illustrate side views of multiple different embodiments of the cross-linked gel 10 when cured. In FIG. 2A, a cross-linked gel 10A is shown having two tiers, a first tier 20 and a second tier 22. The first tier 20 and the second tier 22 as shown are formed of different materials. The different materials can be different forms of fish oil, different naturally occurring oils other than fish oil, or therapeutic components as will be discussed later herein. The different materials bind together to form the cross-linked gel 10A.

FIG. 2B shows a cross-linked gel 10B having a first tier 24, a second tier 26, and a third tier 28. In the embodiment shown, each of the tiers 24, 26, and 28 is formed of the same material. The plurality of tiers indicates the ability to create a thicker cross-linked gel 10 if desired. The greater the number of tiers, the thicker the resulting gel. The thickness of the cross-linked gel 10 can have an effect on the overall strength and durability of the cross-linked gel 10. A thicker gel is generally stronger and more durable. In addition, the thickness of the cross-linked gel 10 can also affect the duration of time that the cross-linked gel 10 lasts after implantation. A thicker cross-linked gel 10 provides more material to be absorbed by the body, and thus will last longer than a thinner cross-linked gel 10. One of ordinary skill in the art will appreciate that the thickness of the cross-linked gel 10 can vary both by varying the thickness of each tier 24, 26, and 28, and by varying the number of tiers 24, 26, and 28. Accordingly, the present invention is not limited to the particular layer combinations illustrated.

FIG. 2C shows another cross-linked gel 10C, having four tiers, a first tier 30, a second tier 32, a third tier 34, and a fourth tier 36. In this example embodiment, the first tier 30 and the third tier 34 are formed of the same material, while the second tier 32 and the fourth tier 36 are formed of a material different from each other and different form that of the first tier 30 and the third tier 34. Accordingly, this embodiment illustrates the ability to change the number of tiers, as well as the material used to form each of the tiers 30, 32, 34, and 36. Again, the different materials can be derived from different forms of fish oil, different naturally occurring oils other than fish oil, or therapeutic components as will be discussed later herein.

FIGS. 3A through 3F show additional embodiments or configurations of the cross-linked gel 10. The embodiments include cross-linked gel 10D in a circular configuration, cross-linked gel 10E in an oval configuration, cross-linked gel 10F in a U-bend configuration, cross-linked gel 10G in a square configuration having a circular aperture, cross-linked gel 10H in a wave configuration, and cross-linked gel 10I in an irregular shape configuration. Each of the configurations of the cross-linked gel 10D through 10I represent different types of configurations. The configurations illustrated are by no means the only possible configurations for the cross-linked gel 10. One of ordinary skill in the art will appreciate that the specific shape or configuration of the cross-linked gel 10 can vary as desired. A more prevalent configuration is the rectangular or oblong configuration of FIG. 1. However, FIGS. 3A through 3F illustrate a number of different alternative embodiments, and indicate some of the many possible configurations.

Figure 4:
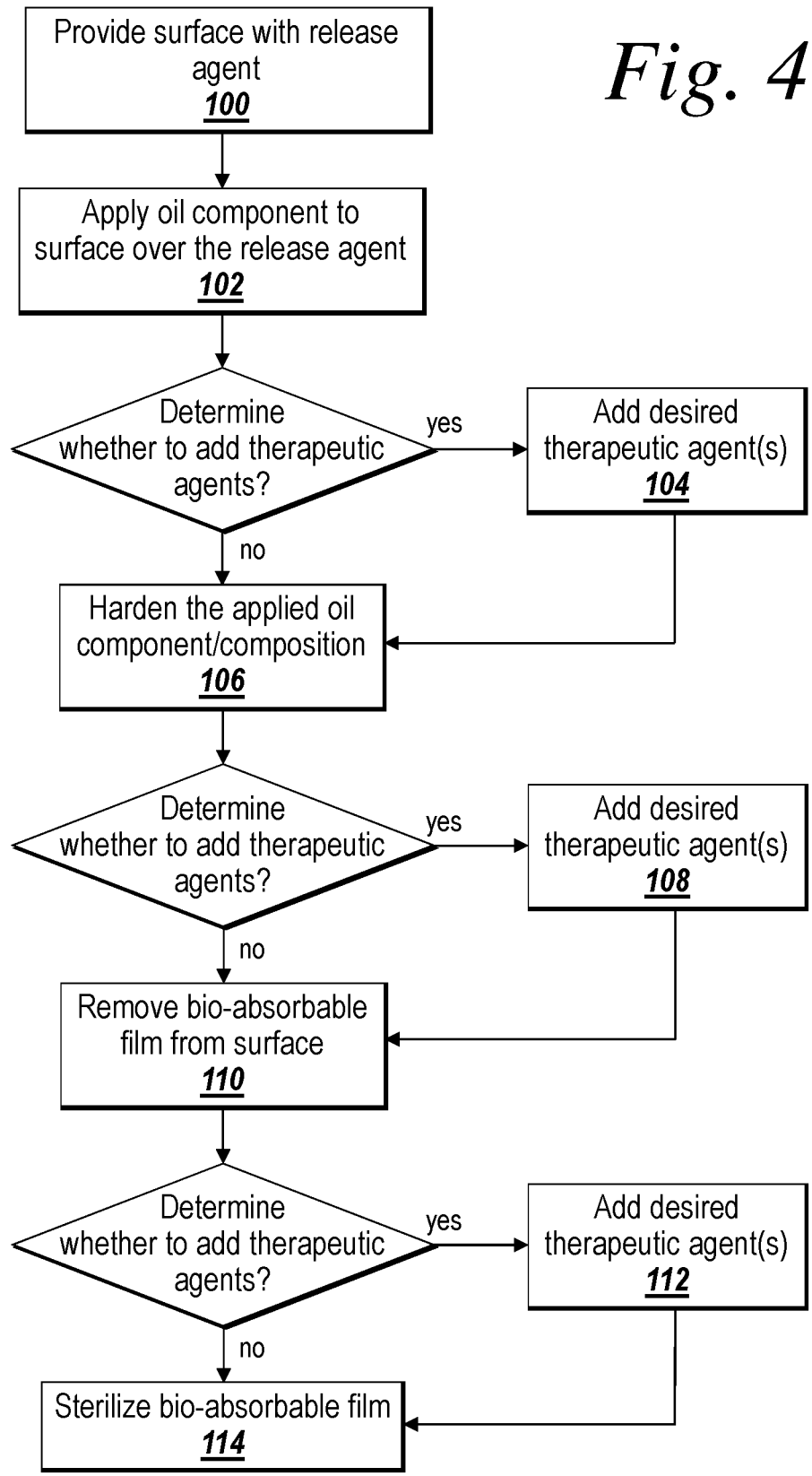
FIG. 4 is a flow chart illustrating a method of making the cross-linked gel of the present invention, in accordance with one embodiment of the present invention.

FIG. 4 is a flowchart illustrating one example method for the formation of the cross-linked gel 10. A surface is provided having a release agent (step 100). The surface can be prepared by the application of the release agent, or the release agent can be pre-existing. The release agent can be a number of different solutions, including for example, polyvinyl alcohol (PVA). The release agent can be applied in a number of different ways as well, including but not limited to spraying, dipping, coating, painting, and the like. It should be noted that the release agent can be applied to the surface immediately prior to the remaining steps or well in advance of the remaining steps, so long as when the remaining steps are executed there is a release agent on the surface.

An oil component is applied to the surface on top of the release agent (step 102). As noted previously, the oil component can be a naturally occurring oil, such as fish oil, cod liver oil, cranberry oil, or other oils having desired characteristics. In addition, the oil component can be an oil composition, meaning a composition containing oil in addition to other substances. For example, the oil composition can be formed of the oil component in addition to a solvent and/or a preservative. Solvents can include a number of different alternatives, including ethanol or N-Methyl-2-Pyrrolidone (NMP). The preservative can also include a number of different alternatives, including vitamin E compounds. One of ordinary skill in the art will appreciate that there are a number of different solvents and preservatives available for use with the oil component to form the oil composition, and as such the present invention is not limited to only those listed in the examples herein. The solvent can be useful to alter the physical properties of the oil, as well as prepare the oil for combination with a therapeutic agent as described below. The preservative can also be useful in altering the physical properties of the oil component, as well as protecting some of the beneficial properties of the oil component during certain curing processes. Such beneficial properties include the healing and anti-inflammatory characteristics previously mentioned.

The oil component can be combined with one or more therapeutic agents to form an oil composition. Thus, if the added therapeutic benefit of a particular therapeutic agent or agents is desired, the therapeutic agent(s) can be added to the oil component prior to application to the surface, along with the oil component during application to the surface (including mixing with the oil component prior to application), or after the oil component has been applied (step 104). The different alternatives for adding the therapeutic agent(s) are determined in part based on the desired effect and in part on the particular therapeutic agent(s) being added. Some therapeutic agents may have reduced effect if present during a subsequent curing step. Some therapeutic agents may be more useful intermixed with the oil component to extend the release period, or applied to the surface of the oil component, resulting in a faster release because of increased exposure. One of ordinary skill in the art will appreciate that a number of different factors, such as those listed above in addition to others, can influence when in the process the therapeutic agent is added to the oil component, or the cross-linked gel 10. Accordingly, the present invention is not limited to the specific combinations described, but is intended to anticipate all such possible variations for adding the therapeutic agent(s).

For example, if 80% of a therapeutic agent is rendered ineffective during curing, the remaining 20% of therapeutic agent, combined with and delivered by the barrier can be efficacious in treating a medical disorder, and in some cases have a relatively greater therapeutic effect than the same quantity of agent delivered with a polymeric or other type of coating or barrier. This result can be modified with the variance of alpha-tocopherol to protect the therapeutic agent during the curing process, and then slow and extend the delivery of the therapeutic agent during absorption of the barrier layer into the tissue.

The oil component (or composition if mixed with other substances) is then hardened into the cross-linked gel 10 (step 106). The step of hardening can include hardening, or curing, such as by introduction of UV light, heat, oxygen or other reactive gases, chemical curing, or other curing or hardening method. The purpose of the hardening or curing is to transform the more liquid consistency of the oil component or oil composition into a more solid film or gel, while still maintaining sufficient flexibility to allow bending and wrapping of the film or gel as desired. However, the hardening process as described herein does not refer to or include the process of hydrogenation.

After the cross-linked gel 10 has formed, another determination is made as to whether therapeutic agents should be applied to the gel. If desired, the therapeutic agent(s) is added to the cross-linked gel 10 (step 108). Subsequently, the cross-linked gel 10 is removed from the surface (step 110). Once again, there is opportunity to apply a therapeutic agent(s) to the cross-linked gel 10 on one or both sides of the cross-linked gel 10. If such therapeutic agent(s) is desired, the therapeutic agent(s) is applied (step 112). The additional therapeutic agent can also be applied in the form of a non-cured or minimally cured oil, such as fish oil. The oil can likewise include other therapeutic agents mixed therewith. The resulting structure of such an application forms the underlying cross-linked gel 10 that is cured to form the film or gel, with a top coating of oil and potentially additional therapeutic agent layered on top. This structure enables the provision of a short term release of therapeutic from the oil top layer combined with a longer term release from the cured gel, which takes more time to degrade.

After application of the therapeutic agent(s), or after the cross-linked gel 10 is removed from the surface, the cross-linked gel 10 is sterilized. The sterilization process can be implemented in a number of different ways. For example, sterilization can be implemented utilizing ethylene oxide, gamma radiation, E beam, gas plasma, or vaporized hydrogen peroxide (VHP). One of ordinary skill in the art will appreciate that other sterilization processes can also be applied, and that those listed herein are merely examples of sterilization processes that result in a sterilization of the cross-linked gel 10, preferably without having a detrimental effect on the cross-linked gel.

It should be noted that the oil component or oil composition can be added multiple times to create multiple tiers in forming the cross-linked gel 10. For example, if a thicker cross-linked gel 10 is desired, additional tiers of the oil component or oil composition can be added after steps 100, 104, 106, 108, 110, or 112. Different variations relating to when the oil is hardened and when other substances are added to the oil are possible in a number of different process configurations. Accordingly, the present invention is not limited to the specific sequence illustrated. Rather, different combinations of the basic steps illustrated are anticipated by the present invention.

Figure 5A:
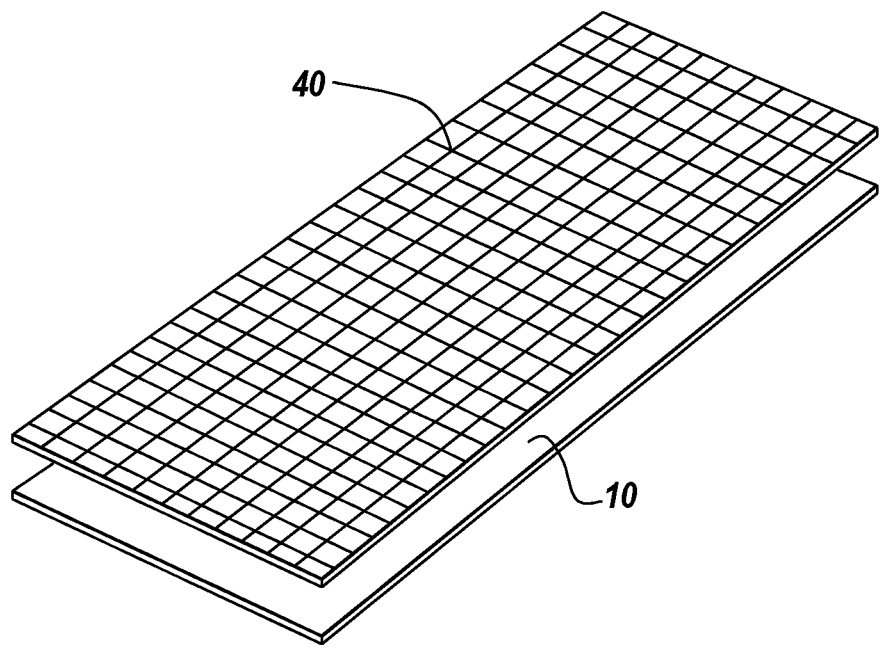
FIGS. 5A and 5B are perspective and cross-sectional views of the cross-linked gel in combination with a medical device, in accordance with one embodiment of the present invention.
Figure 5B:
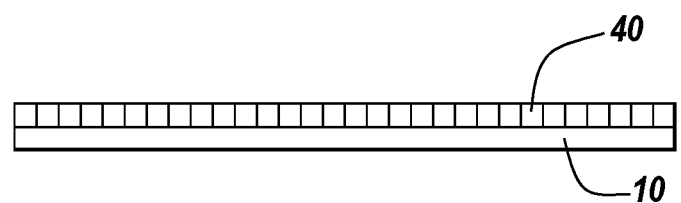

FIGS. 5A and 5B illustrate the cross-linked gel 10 and a medical device in the form of a mesh 40. In FIG. 5A, the cross-linked gel 10 and mesh 40 are shown in exploded view, while FIG. 5B shows the cross-linked gel 10 coupled with the mesh 40. The mesh 40 is merely one example medical device that can be coupled with the cross-linked gel 10. In the instance of the mesh 40, it can be useful to have one side of the mesh support a rougher surface to encourage tissue in-growth, and the other side of the mesh with an anti-adhesion, non-inflammatory, and/or anti-inflammatory surface to prevent the mesh from injuring surrounding tissue or causing inflammation. The coupling of the cross-linked gel 10 with the mesh 40 achieves such a device.

As understood by one of ordinary skill in the art, the properties of the mesh 40 and the cross-linked gel 10 can vary. There may be a requirement for the mesh 40 to have one side, or a portion of a side, that has anti-adhesion properties for a period of several days. Alternatively, multiple sides of the mesh 40 may be required to have anti-adhesion properties. As such, the cross-linked gel 10 can be applied to all sides, or portions of sides, or portions of one side of the mesh 40.

In addition, the requirement may be for the anti-adhesion properties to last several weeks, or even longer. Accordingly, the rate of degradation can also be varied by changing such properties as amount of cross-linking, thickness, and existence of additives, such as vitamin E compounds to achieve longer or shorter term anti-adhesion properties. In addition, there may be a desire to include a therapeutic agent to reduce inflammation, provide antibiotic therapy, or other therapeutic measures, in combination with the use of the mesh 40. Accordingly, the therapeutic agent(s) can be added to the cross-linked gel 10 to achieve the desired controlled release of the therapeutic agent after implantation. As previously described, combinations of cured oils top coated with lesser cured or non-cured oils and therapeutic agents can form the cross-linked gel 10.

The particular properties or characteristics of the mesh 40 are determined based on the desired use of the mesh 40. A common implementation is for the mesh 40 to be formed of a bio-compatible material, such as polypropylene, however other bio-compatible materials can be utilized, such as a mesh formed of the same or similar substance as the cross-linked gel 10 (i.e., oil based).

Figure 6:
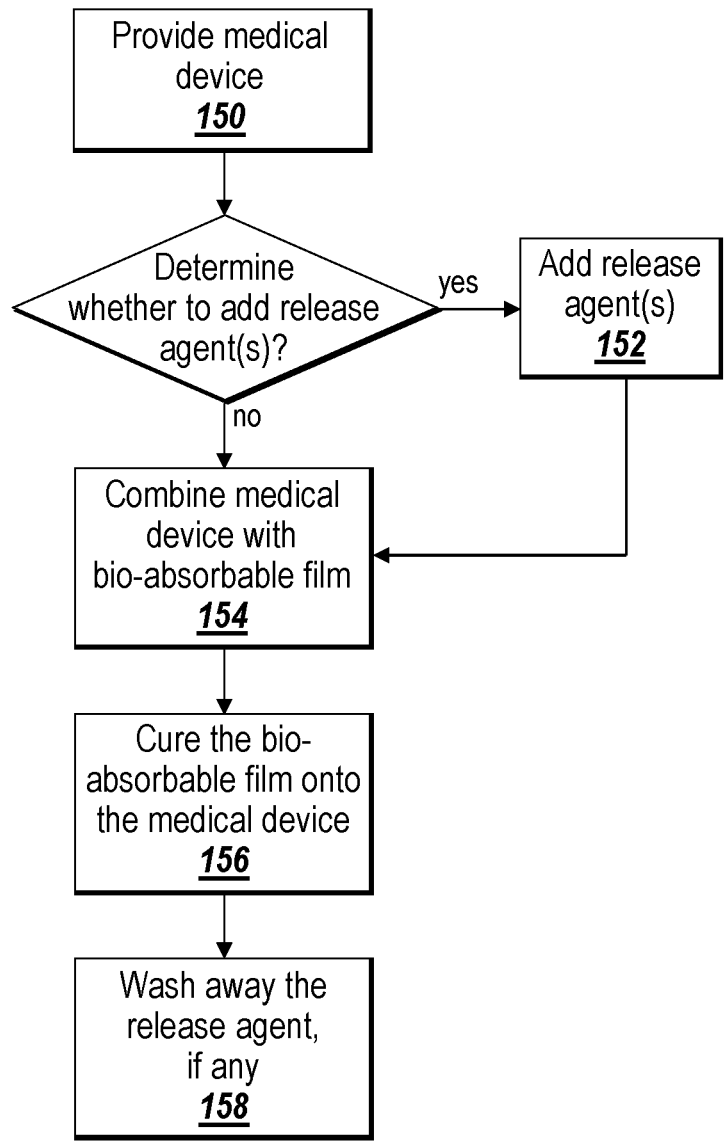
FIG. 6 is a flow chart illustrating a method of combining the cross-linked gel with a medical device, in accordance with one embodiment of the present invention.
Figure 8A:
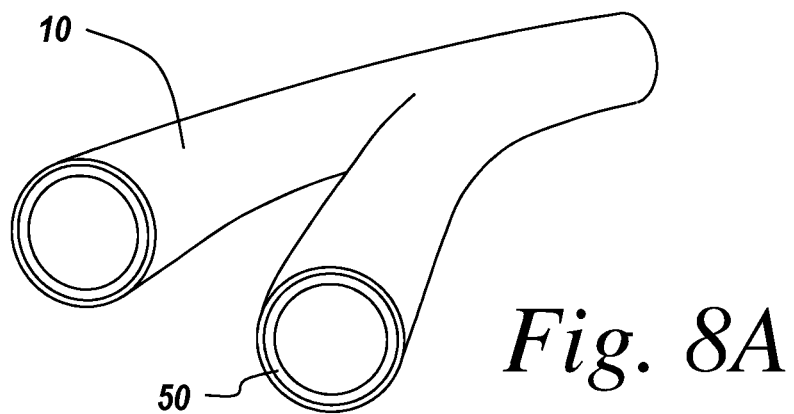
FIGS. 8A, 8B, and 8C are diagrammatic illustrations of the barrier coupled with various medical devices.
Figure 8B:
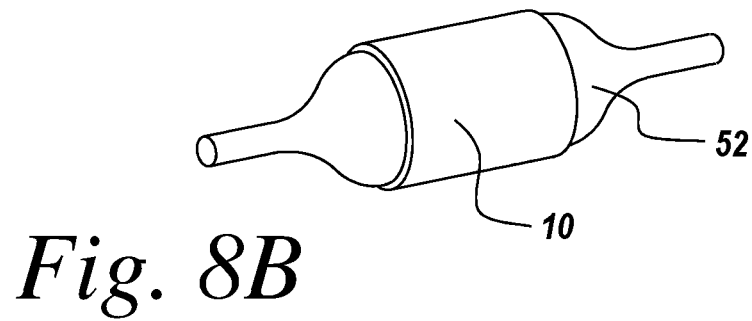
Figure 8C:
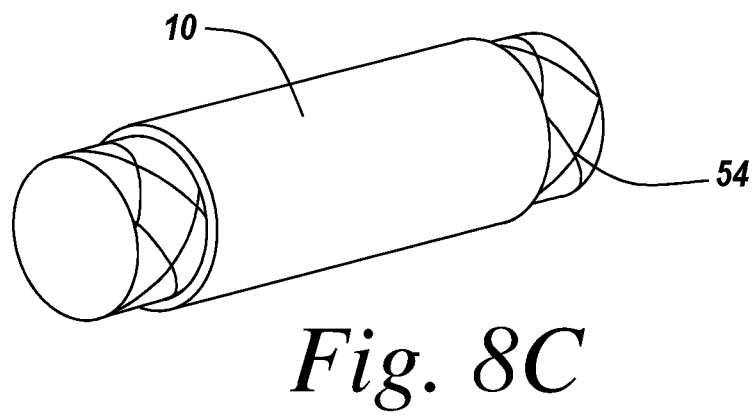

FIG. 6 is a flowchart illustrating one example method for forming the mesh 40 and cross-linked gel 10 combination. The medical device is provided (step 150). The medical device can be, for example, the mesh 40, or a graft 50, a catheter balloon 52, a stent 54, as shown in FIGS. 8A through 8C, or another form of medical device as would be understood by one of ordinary skill in the art.

A determination is made as to whether a release agent should be added to the medical device to aid in removing the device from its location (e.g., on a surface) after combination with the cross-linked gel 10. If a release agent is required, the release agent is applied to the medical device (step 152). An example release agent for such an application is polyvinyl alcohol.

The medical device is then combined with the cross-linked gel 10 (step 154). Depending on the particular medical device, the combination with the cross-linked gel 10 can be implemented more efficiently by either applying the cross-linked gel 10 to the medical device, or placing the medical device on the cross-linked gel 10. For example, in the case of the mesh 40, the mesh 40 can be placed on top of the cross-linked gel 10, or the cross-linked gel 10 can be placed on top of the mesh 40.

The medical device and the cross-linked gel are then cured to create a bond (step 156). The curing process can be one of several known processes, including but not limited to applying heat, or UV light, or chemical curing, to cure the cross-linked gel. After curing, if there is any release agent present, the release agent is washed away using water, or some other washing agent (step 158).

Figure 7:
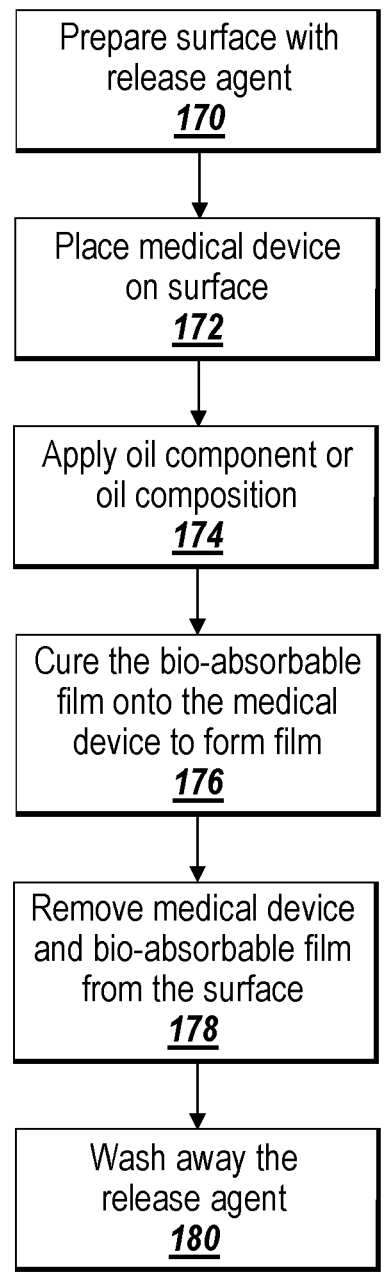
FIG. 7 is a flow chart illustrating another variation of the method of FIG. 6, in accordance with one embodiment of the present invention.

FIG. 7 is a flowchart illustrating another example method of forming a medical device with a cross-linked gel. A surface is prepared with a release agent, such as PVA (step 170). The medical device is placed on the surface (step 172). The oil component or oil composition is applied to the medical device (step 174). The oil component or oil composition can be, for example, poured or sprayed onto the medical device. The combined oil component/composition and medical device are then cured (step 176) using methods such as application of heat, UV light, oxygen, chemical cross-linker, or hardening processes, to form the cross-linked gel in combination with the medical device. The combined cross-linked gel and mesh are then removed from the surface (step 178) and the release agent is washed away (step 180).

As with the method of FIG. 6, if desired, a therapeutic agent can be added to the oil component or oil composition at any point along the process forming the combined cross-linked gel 10 and medical device, including being a component of the oil composition. As discussed previously, consideration must be given as to whether the therapeutic agent may be affected by the curing process, or other aspects of the process.

Furthermore, the formation of the oil composition can be done in accordance with different alternatives to the methods described. For example, prior to forming the cross-linked gel 10, a preservative, such as a Vitamin E compounds can be mixed with the naturally occurring oil component to form the oil composition. A solvent can be mixed with a therapeutic agent, and then added to the naturally occurring oil to form the oil composition. The solvent can be chosen from a number of different alternatives, including ethanol or N-Methyl-2-Pyrrolidone (NMP). The solvent can later be removed with vacuum or heat. Other solvent alternatives can include, but are not limited to, a solvent or mixture of solvents including solvents that are generally acceptable for pharmaceutical use. Suitable solvents include, for example: alcohols and polyols, such as $C_2$-$C_6$ alkanols, 2-ethoxyethanol, ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, and polypropylene glycol; amides, such as 2-pyrrolidone, 2-piperidone, 2-caprolactam, N-alkylpyrrolidone, N-methyl-2-pyrrolidone, N-hydroxyalkylpyrrolidone, N-alkylpiperidone, N-alkylcaprolactam, dimethylacetamide; esters, such as ethyl acetate, methyl acetate, butyl acetate, ethylene glycol diethyl ether, ethylene glycol dimethyl ether, propylene glycol dimethyl ether, ethyl proprionate, tributylcitrate, acetyl triethylcitrate, acetyl tributyl citrate, triethylcitrate, ethyl oleate, ethyl caprylate, ethyl cutyrate, tracetin, ε-caprolactone and isomers thereof, δ-valerolactorne and isomers thereof, β-butyrolactone and isomers thereof; and other solvents, such as water, dimethylsulfoxide, benzyl benzoate, ethyl lactate, acetone, methylethyl ketone, dimethylsolfone, tetrahydrofuran, decylmethylsufoxide, N,N-diethyl-m-toulamide or 1-dodecylazacycloheptan-2-one, hexane, chloroform, dichloromethane.

In addition, it should again be noted that the oil component or oil composition can be added multiple times to create multiple tiers in forming the cross-linked gel 10. If a thicker cross-linked gel 10 is desired, additional tiers of the oil component or oil composition can be added after steps 174 and 176. Different variations relating to when the oil is hardened and when other substances are added to the oil are possible in a number of different process configurations. Accordingly, the present invention is not limited to the specific sequence illustrated. Rather, different combinations of the basic steps illustrated are anticipated by the present invention.

Depending on the type of therapeutic agent component, the resulting cross-linked gel 10 can maintain its bio-absorbable characteristics if the therapeutic agent component is also bio-absorbable.

The therapeutic agent component, as described herein, has some form of therapeutic or biological effect. The oil component or oil composition component can also have a therapeutic or biological effect. Specifically, the cross-linked gel 10 (and its oil constituents) enable the cells of body tissue of a patient to absorb the cross-linked gel 10 itself, rather than breaking down the gel and disbursing by-products of the gel for ultimate elimination by the patient's body.

As previously stated, and in accordance with embodiments of the present invention, the cross-linked gel 10 is formed of a naturally occurring oil, or composition including a naturally occurring oil, such as fish oil, cod liver oil, cranberry oil, and the like. A characteristic of the naturally occurring oil is that the oil includes lipids, which contributes to the lipophilic action described later herein, that is helpful in the delivery of therapeutic agents to the cells of the body tissue. In addition, the naturally occurring oil can include the essential omega-3 fatty acids in accordance with several embodiments of the present invention.

It should also be noted that the present description makes use of the mesh 40 as an example of a medical device that can be combined with the cross-linked gel 10 of the present invention. However, the present invention is not limited to use with the mesh 40. Instead, any number of other implantable medical devices can be combined with the cross-linked gel 10 in accordance with the teachings of the present invention. Such medical devices include catheters, grafts, balloons, prostheses, stents, other medical device implants, and the like. Furthermore, implantation refers to both temporarily implantable medical devices, as well as permanently implantable medical devices.

FIGS. 8A, 8B, and 8C illustrate some of the other forms of medical devices mentioned above in combination with the cross-linked gel 10 of the present invention. FIG. 8A shows a graft 50 with the cross-linked gel 10 coupled or adhered thereto. FIG. 8B shows a catheter balloon 52 with the cross-linked gel 10 coupled or adhered thereto. FIG. 8C shows a stent 54 with the cross-linked gel 10 coupled or adhered thereto. Each of the medical devices illustrated, in addition to others not specifically illustrated or discussed, can be combined with the cross-linked gel 10 using the methods described herein, or variations thereof. Accordingly, the present invention is not limited to the example embodiments illustrated. Rather the embodiments illustrated are merely example implementations of the present invention.

Example #1

An embodiment of the present invention was implemented in a rat model to demonstrate the performance of the cross-linked gel of the present invention relative to other known surgical mesh devices. The devices were implanted in a rat to repair abdominal wall defects. Healing characteristics, adhesion formation and tenacity, and inflammatory response associated with these materials were compared.

A polypropylene mesh material (ProLite™) provided by Atrium Medical Corporation of Hudson, N.H., coated with one embodiment of the cross-linked gel described herein. The polypropylene mesh with cross-linked gel was compared with a bare polypropylene control mesh, and DualMesh® biomaterial provided by W. L. Gore & Associates, Inc.

Five samples of each mesh type were implanted according to a random schedule. On the day of surgery, the animals were anesthetized with an injection of 50 mg/kg Nembutal IP. The animal was prepped for surgery, and a midline abdominal incision was made. A portion of rectus muscle and fascia was removed leaving an approximately 20 mm×30 mm full thickness defect in the abdominal wall. Using 4-0 Prolene, the appropriate patch was sutured into place repairing the existing defect. An overlap of mesh was placed over the defect to ensure proper repair, with the mesh samples being 2.5 cm×3.5 cm in size. The mesh was placed such that the smoother side was toward the viscera in the case of the polypropylene mesh with cross-linked gel, and the appropriate side of the Gore DualMesh was also placed towards the viscera. Suture knots were made on the abdominal wall side of the implant rather than the visceral side as to not interfere with tissue attachment. The mesh was sutured around the entire perimeter to ensure adequate placement. The subdermal and subcutical layers were closed with Vicryl. The skin was closed using surgical staples. The animals received Buprenorphine for pain. The mesh was explanted at approximately 30 days.

Sample Explantation:

Approximately 30 days after implantation, the animals were again anesthetized for explant of the mesh samples. The skin staples were removed, and a vertical incision through the skin and subcutaneous tissue was made lateral to both the implantation site and patch. Through this incision, the implant was inspected and photos were taken to document adhesion formation. Upon gross examination, the same investigator evaluated each sample for adherent intraperitoneal tissues and assigned an adhesion grade to each sample (Jenkins S D, flamer T W, Parteka J J, and Condon R E. A comparison of prosthetic materials used to repair abdominal wall defects. Surgery 1983; 94:392-8). In general, the adhesions were scored as: 0—no adhesions; 1—minimal adhesions that could be freed by gentle blunt dissection; 2—moderate adhesions that could be freed by aggressive blunt dissection; 3—dense adhesion that require sharp dissection.

Once the gross evaluation was complete, the mid-portion of the abdominal cavity was excised including the implant, and adhesive tissue not completely separated from the implant, and the overlying subcutaneous and skin. Sections were then fixed and processed for histological evaluation. The histology samples were stained with Hematoxylin and Eosin, Trichrome, GS1, and Vimentin.

Polypropylene Mesh Control:

These patches had a mean adhesion score of 2.1. Adhesions consisted of omentum, epididymal fat, and one had intestinal adhesions. Many of the adhesions were at the edges of the patch/tissue interface. The adhesions required aggressive blunt dissection to remove them. There was a moderate inflammatory response associated around the fibers of the mesh. There was a tight association of fat to the implant surface on the peritoneal cavity side, meaning the adhesions were not fully removed.

Gore DualMesh® Control:

Patches were entirely covered with adhesions. The adhesions consisted of epidiymal fat, omentum and bowel. The mean adhesion score was 2.9. There was a capsule covering the entire patch that needed sharp dissection to free from material. Adhesions pulled free from capsule with blunt dissection. A moderate to severe inflammatory response was observed in association with the skin side of the implant. The thin fibrous capsule on the peritoneal side of the implant was avascular and in some implants was loosely adherent to associated tissue.

Polypropylene Mesh with Cross-Linked Gel (Embodiment of Present Invention):

These patches had a mean adhesion score of 1.6. Adhesions included epididymal fat and some omentum. The adhesions dissociated from the patches relatively easily. There was a mild to minimal inflammatory response associated with the exposed polypropylene fibers of this material. Vimentin staining showed a layer of mesothelial cells formed on the tissue on the peritoneal cavity side of the implant.

The polypropylene mesh with cross-linked gel in accordance with one embodiment of the present invention showed good results in terms of adhesion minimization, tenacity of adhesions formed, and a low inflammatory response. The coated mesh product was also easy to handle, place, and suture for repair of an abdominal wall defect in this model.

Returning to the step of curing as described herein, the step can have a number of different variations and permutations that ultimately influence the properties of the resulting cured cross-linked gel, and any therapeutic agents if include therein. In this instance making use of a naturally occurring oil, such as fish oil, such oils or oil compositions as described herein can be heated to increase viscosity. The temperature, time duration, and volume of airflow over the oil or oil composition will affect how viscous the oil or oil composition becomes.

In addition, combining pre-cured, highly viscous oil with untreated oil results in a faster cure time of the resulting combination when forming the cross-linked gel. Also, taking a pre-cured oil and decreasing its viscosity slightly with solvent will result in a faster cure time as well. To demonstrate some of the possible variations of time and temperature, the following Examples #2 through #4 are provided.

Example #2

Two samples of pre-cured fish oil were prepared. Epax 3000TG fish oil (with a starting viscosity of 40 Cps) was weighed out in two 57 mm weigh pans at 5 grams (Sample C) and 3 grams (Sample D). Both pans were heated at 150° F. for 70 hours. The resulting viscosities were: 1,500 Cps for Sample C and 14,000 Cps for Sample D (3 grams), respectively. Both of the thickened oils were mixed with non-cured oil at 25% ratio. These mixtures were used to coat polypropylene mesh against a control of non-cured oil. Once mesh was coated, it was placed on a curing substrate, Teflon®. The mesh samples were heated at 200° F. for 17 hours and checked. Both thickened samples were cured in 17 hours, displaying less "tackiness" than the control sample (which usually cures in 24 hours).

Example #3

Sample D, at a viscosity of 14,000 Cps was mixed with 99% Isopropyl Alcohol, to decrease its viscosity in a ratio of 66% oil to 33% solvent. This mixture was then used to coat polypropylene mesh. A control of non-cured oil was used as a comparison. Once the mesh samples were coated, they were placed on a Teflon® curing substrate and heated at 200° F. An initial check was done at 15 hours. Sample D was cured (dry) better than the control at the same amount of time. In fact, this sample was more cured than the control at 24 hours in 200° F. oven.

Example #4

Thickened oil (Sample C having a viscosity of about 1,500 Cps) was used to coat polypropylene mesh. This oil was not cut with a solvent. A control of non-cured fish oil coated mesh was used as a comparison. Both coated mesh samples were placed on a Teflon® curing substrate and heated at 200° F. After 15 hours, the samples were checked. The thickened oil Sample C had a slight inconsistent coating due to its start viscosity; however, the sample was more cured (displaying much less tackiness) than the control sample at the same time. In fact, Sample C was more cured than the control at 24 hours in 200° F. oven.

Modifying the starting pre-cured viscosity or pre-cured oil concentration in the mixture will enhance the curing speed. In addition, alternate methods of curing can be used in a similar manner (i.e. heat, UV, IR, and the like) and the sample will cure sooner than without pre-curing the oil. One of ordinary skill in the art will appreciate that the scope of the present invention is not limited to only coating on the mesh, but rather has application to other medical devices, or as a stand-alone film.

The curing conditions utilized, such as the duration of time and the degree of temperature, directly influence the amount of cross-linking that occurs in the cross-linked gel (i.e., the cross-link density). Cured fish oil coatings enable regulation of the release profile of drug-loaded oil-based coatings from implantable devices. The release profile can be controlled through changes in oil coating chemistry by varying coating composition, temperature, and cure times. The position of the drug-containing layer on the coated device provides an additional mechanism to alter the release profile of the drug-loaded fish oil coating. This can be achieved by either loading the drug into the encapsulating base layer of the device, or by coating a topcoat overlayer coating onto the previously cured encapsulating base layer.

More specifically, curing conditions utilized to form the cross-links, such as time and temperature, directly influence the amount of coating cross-linking density and byproduct formation, which in turn effects the coating degradation. Thus, by altering the curing conditions employed, the dissolution rate of the therapeutic compound of interest is also altered. The effects of curing conditions on fish oil curing chemistry and drug release properties are demonstrated in the following examples.

Example #5 (the Effects Time and Temperature on Cured Fish Oil Chemistry)

Two different curing profiles were provided to demonstrate the effects of curing temperature and time on the chemistry of the cured fish oil coatings. Atrium® ProLite Ultra™ polypropylene mesh was coated with Epax 3000TG fish oil and oven cured. The conditions were 200° F. for 24 hrs and 150° F. for 3 days.

FTIR analysis showed that curing at 150° F. for 3 days resulted in a 36% reduction in the anhydride/aliphatic peroxide/lactone cross-linking, 25% increase in the trans C=C bonds, and a 10% decrease in the amount of fatty acid/ketone byproducts formed compared to samples that were cured at 200° F. for 24 hours.

DSC analysis was performed on 150° F. and 200° F. cured fish oil coatings that were extracted in THF for 3 hrs at 37° C. to isolate the soluble (soluble oxidized byproducts, i.e. fatty acid, ketone, alcohols, etc.) and insoluble (cross-linked fatty acid and glyceride molecules) components of the mesh coating. Gravimetric analysis showed that the 200° F. coating consisted of a 50:50 mix of soluble:insoluble coating components, where as the 150° F. sample had a ratio of 62:38 soluble:insoluble coating components. DSC analysis of the insoluble components of the coatings showed that the 200° F. and 150° F. insoluble coating components were 93% and 70% cured, respectively. DSC analysis of the soluble components of the coatings showed that the 200° F. coating possessed less long chained oxidized byproducts than the 150° F. coating.

These above described examples are illustrative of the fact that coatings cured at 200° F. are relatively more cross-linked and further cured than 150° F. coatings.

Example #6 (The Effects Time and Temperature on Cured Fish Oil Degradation Rate)

The cross-link density and chemistry of the coating affects its degradation properties. FTIR analysis of the cured fish oil coating shows that the cured coating is formed of primarily ester bonds in addition to lesser amounts of anhydride, lactone, and aliphatic peroxide bonds that will undergo hydrolysis and degrade into smaller components over time. To demonstrate the differences in the 150° F. and 200° F. cured fish oil coating degradation behavior, both cured fish oil encapsulated mesh samples were placed in 0.1 M sodium phosphate buffer containing 0.1 M sodium chloride solution at pH=7.4 at either 37° C. or 55° C. The 200° F. cured fish oil coating dissolved during an 18-day period at 55° C., where it took 12 weeks to dissolve at 37° C. The 150° F. cured fish oil coating dissolved during an 18-21 day period at 55° C., where ongoing degradation at 37° C. demonstrates the coating to be partially dissolved after 21 days.

These results show that both the 200° F. and 150° F. cured fish oil coatings dissolve into solution using a hydrolysis mechanism.

Example #7 (the Effects of Time and Temperature on the Release of Therapeutics from Cured Fish Oil Coatings)

Model drug delivery demonstrations were performed using coatings cured at 200° F. for 24 hours or 150° F. for 3 days. All samples were 1×1" and dissolution was performed in 0.01 M PBS solution. All drug samples were loaded as an encapsulated mesh coating created by mixing the liquid fish oil and drug together, with or without solvent, followed by coating a piece of bare mesh and curing using either the 150° F. or 200° F. curing conditions described herein.

Demonstrating the delivery of an anti-inflammatory drug, a comparison of pure fish oil encapsulated mesh coatings was performed, using the 150° F. curing method and the 200° F. curing method. An amount of about 2.4% of anti-inflammatory drug remained in the fish oil after the nMP solvent was removed. The anti-inflammatory drug and the fish oil were cured at either 200° F. for 24 hours or 150° F. for 3 days. Based on an HPLC analysis, the initial drug loading after curing was about 442 ug (14.84% recovery) for the sample cured at 200° F. and about 238 ug (10.97% recovery) for the sample cured at 150° F. The amount of drug released over time measured in days is shown in Graph #1, illustrated as FIG. 10.

These results show that the 150° F. cured coating, which has less cross-linking, results in a faster drug release than the 200° F. cured coating, which possess more cross-linking. This example demonstrates the ability to load an anti-inflammatory into cured fish oil encapsulated coatings, and alter the drug dissolution release profile by using temperature to control the cross-linking properties of that coating.

Demonstrating the delivery of an anti-proliferative drug, cyclosporine, a comparison of pure fish oil encapsulated mesh coatings was performed, using the 150° F. curing method and the 200° F. curing method. An amount of about 2.84% of anti-proliferative drug (cyclosporine) was in the fish oil; no solvent was used because the cyclosporine was soluble in the fish oil with slight heat at 37° C. The anti-proliferative drug and the fish oil were cured at either 200° F. for 24 hours or 150° F. for 3 days. Based on an HPLC analysis, the initial drug loading after curing was about 478 ug (14.22% recovery) for the sample cured at 200° F. and about 1158 ug (26.00% recovery) for the sample cured at 150° F. The amount of drug released over time measured in days is shown in Graph #2, illustrated as FIG. 11.

These results confirm that the 150° F. cured coating, which has less cross-linking, results in a faster drug release than the 200° F. cured coating, which possess more cross-linking. This example demonstrates the ability to load an anti-proliferative, Cyclosporine A, into cured fish oil encapsulated coatings and alter the drug dissolution release profile by using temperature to control the cross-linking properties of that coating.

Figure 9:
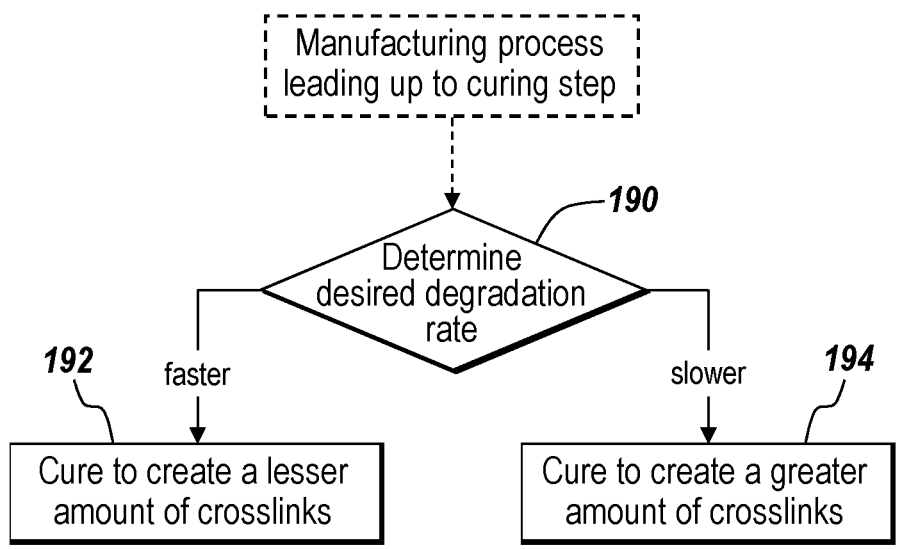
FIG. 9 is a flow chart illustrating one example method of curing to form the cross-linked gel.
Figure 10:
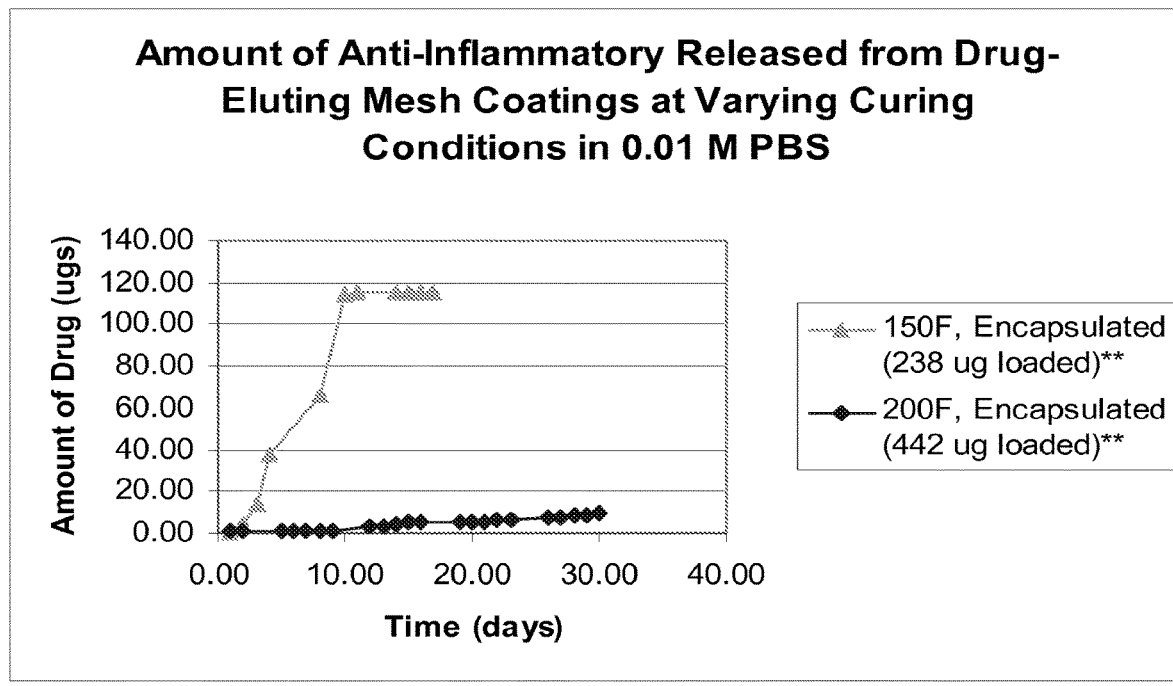
FIG. 10 illustrates the amount of anti-inflammatory drug released over time in 0.01M PBS from drug-eluting mesh fish oil coatings that were exposed to varying curing conditions. The ** indicates that the amount of drug recovered is dependent on the coating weight and amount of drug detected using HPLC methods after drug extraction from the cured fish oil coating.
Figure 11:
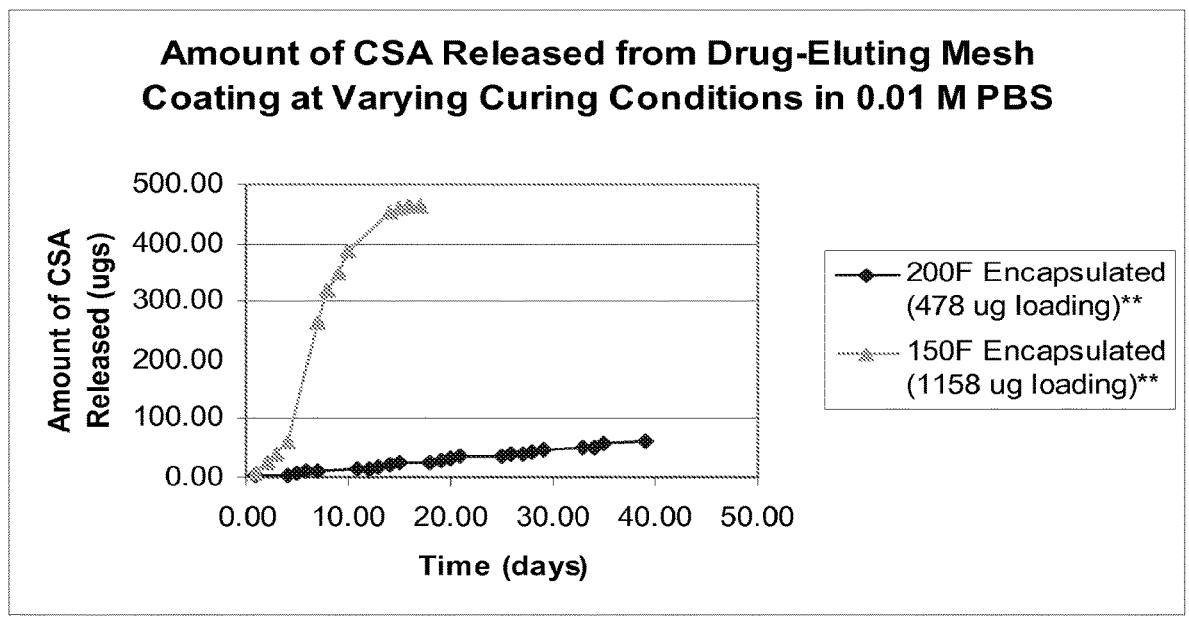
FIG. 11 illustrates the amount of cyclosporine (CSA) released over time in 0.01M PBS from drug-eluting mesh fish oil coatings that were exposed to varying curing conditions. The ** indicates that the amount of drug recovered is dependent on the coating weight and amount of drug detected using HPLC methods after drug extraction from the cured fish oil coating.

In view of the above examples, the following method can be implemented to effect different outcomes based on the variance of the curing process. FIG. 9 shows a flowchart in which considerations are made during the curing process to result in a cured or partially cured cross-linked gel that has specific desired characteristics. In accordance with the method of the present invention, the curing process (such as referred to in step 156 in FIG. 6 and step 176 in FIG. 7 of the present description) can be modified to result in different cross-linked gels. At some point in time prior to beginning the curing portion of the process, a determination is made as to whether a relatively fast but shorter term degradation (corresponding to a faster drug release rate when a drug is included) is desired, or a relatively slower but longer term degradation (corresponding to a slower drug release rate when a drug is included) is desired (step 190). If a relatively faster but shorter term drug release rate is desired, a determination is made to cure in a manner that will result in an amount of cross-links relatively lesser than otherwise possible (step 192). If a relatively slower but longer term drug release rate is desired, a determination is made to cure in a manner that will result in an amount of cross-links relatively greater than the shorter term drug release rate amount, and relatively closer to a maximum possible amount of cross-links to form the gel (step 194).

In general, a higher temperature will result in a greater number of cross-links than a lower temperature. Furthermore, in general, a relatively longer duration of cure time will result in a greater number of cross-links than a relatively shorter duration of cure time. However, as evidenced by the examples described herein, a higher temperature but shorter cure time can result in a greater number of cross-links than a lower temperature with a longer cure time. Thus, a more dominating factor in considering the desired amount of cross-links is temperature, and a lesser impacting factor in considering the desired amount of cross-links is the cure time.

The oil component itself, in the form of fish oil for example, can provide therapeutic benefits in the form of reduced inflammation, and improved healing, if the fish oil composition is not substantially modified during the process that takes the naturally occurring fish oil and forms it into the cross-linked gel 10. Some prior attempts to use natural oils as coatings have involved mixing the oil with a solvent, or curing the oil in a manner that destroys the beneficial aspects of the oil. The solvent utilized in the example cross-linked gel 10 embodiment of the present invention (NMP) does not have such detrimental effects on the therapeutic properties of the fish oil. Thus the benefits of the omega-3 fatty acids, and the EPA and DHA substances are substantially preserved in the cross-linked gel of the present invention.

Therefore, the cross-linked gel 10 of the present invention includes the bio-absorbable naturally occurring oil (i.e., fish oil). The cross-linked gel 10 is thus able to be absorbed by the cells of the body tissue. With the present invention, because of the lipophilic action enabled by the bio-absorbable lipid based cross-linked gel 10 of the present invention, the intake by the tissue cells of the cross-linked gel 10, and any therapeutic agent component, is substantially controlled by the cells themselves. In configurations using polymer based materials, the drugs were released at a rate regardless of the reaction or need for the drug on the part of the cells receiving the drug. With the cross-linked gel 10 of the present invention, the cells can intake as much of the cross-linked gel 10, and correspondingly the therapeutic agent, as is needed by the damaged cell requiring treatment.

In addition, the bio-absorbable nature of the cross-linked gel 10 results in the cross-linked gel 10 being completely absorbed over time by the cells of the body tissue. There is no break down of the cross-linked gel 10 into sub parts and substances that are inflammatory and are eventually distributed throughout the body and in some instances disposed of by the body, as is the case with biodegradable synthetic polymer coatings. The bio-absorbable nature of the cross-linked gel 10 of the present invention results in the cross-linked gel 10 being absorbed, leaving only the medical device structure, if the cross-linked gel 10 is not implanted alone. There is no inflammatory foreign body response to the cross-linked gel 10.

In addition, the cross-linked gel 10 provides a lubricious or anti-adhesive surface against tissue. The cross-linked gel 10 itself can provide an anti-adhesion barrier between two sections of tissue, or the cross-linked gel 10 can form an anti-adhesion surface on a medical device, such as the mesh 40. The use of the naturally occurring oil, such as fish oil, provides extra lubrication to the surface of the medical device, which helps to reduces injury. With less injury, there is less of an inflammatory response, and less healing required. Likewise the fatty acid derived cross-linked gel that makes up the cross-linked gel maintains anti-inflammatory properties and non-inflammatory properties, which also substantially lowers the inflammatory response of the tissue. The reduced inflammation also reduces adhesions.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

What is claimed is:

1. A method of forming a cured non-polymeric gel, comprising:
    determining a desired amount of non-polymeric cross-linking desired within an oil or oil composition, the oil or oil composition comprising one or more of eicosapentaenoic acid (EPA), docosahexaenoic acid (DHA), or alpha-linolenic acid (ALA); and
    curing the oil or oil composition with selected curing conditions to achieve a sufficient amount of non-polymeric cross-linking within the oil or oil composition, so as to form the non-polymeric gel, wherein the cured non-polymeric gel comprises a plurality of non-polymeric cross-links resulting from curing the oil or oil composition at the selected curing conditions to achieve the sufficient amount of cross-linking to form the cured non-polymeric gel, wherein the amount of cross-linking is selected based on a desired rate of degradation of the gel after the gel is implanted within a patient.

2. The method of claim 1, wherein the gel further comprises at least one therapeutic agent and the method further comprises releasing the therapeutic agent from the gel at a predetermined rate determined by the curing at the selected curing conditions.

3. The method of claim 1, wherein the oil or oil composition comprises at least one component selected from a group of components consisting of fatty acids, monoglycerides, diglycerides, triglycerides, free fatty acids, and esters of fatty acids.

4. The method of claim 1, wherein the determining comprises selecting the amount of cross-linking based on a desired rate of degradation of the gel following implantation.

5. The method of claim 1, further comprising applying heat: at a selected temperature, for a selected time duration, until a desired viscosity is obtained.

6. The method of claim 5, wherein applying heat includes applying heat at the selected temperature, and the selected temperature is relatively higher if more cross-linking is desired and relatively lower if less cross-linking is desired.

7. The method of claim 5, wherein applying heat includes applying heat at the selected time duration, and the selected time duration is relatively longer if more cross-linking is desired and relatively shorter if less cross-linking is desired.

8. The method of claim 5, wherein the oil or oil composition is configured such that curing at a relatively greater temperature for a relatively lesser amount of time results in a greater amount of cross-linking within the oil or oil composition than curing at a relatively lesser temperature for a relatively greater amount of time.

9. The method of claim 1, wherein a relatively lesser amount of cross-links provides a relatively faster rate of degradation of the gel, while a relatively greater amount of cross-links provides a relatively slower rate of degradation of the gel.

10. The method of claim 1, wherein curing the gel is achieved by applying heat, UV, or a combination of applying heat and UV.

11. The method of claim 1, wherein degradation of the gel is via hydrolysis.

* * * * *